United States Patent
Schneider et al.

(10) Patent No.: US 10,578,632 B2
(45) Date of Patent: Mar. 3, 2020

(54) TRANSPORT DEVICE UNIT FOR A LABORATORY SAMPLE DISTRIBUTION SYSTEM

(71) Applicant: Roche Diagnostics Operations, Inc., Indianapolis, IN (US)

(72) Inventors: Hans Schneider, Schwaikheim (DE); Eugen Lusser, Alpnach Dorf (CH); Marcel Kaeppeli, Merenschwand (CH); Tobias Huber, Backnang (DE); Pius Hermann, Urswil (CH); Matthias Edelmann, Winnenden (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 16/052,737

(22) Filed: Aug. 2, 2018

(65) Prior Publication Data

US 2018/0348245 A1 Dec. 6, 2018

Related U.S. Application Data

(63) Continuation of application No. PCT/EP2017/051534, filed on Jan. 25, 2017.

(30) Foreign Application Priority Data

Feb. 26, 2016 (EP) .................................. 16157587

(51) Int. Cl.
*B65G 54/02* (2006.01)
*G01N 35/04* (2006.01)
*G01N 35/00* (2006.01)

(52) U.S. Cl.
CPC ............. *G01N 35/04* (2013.01); *B65G 54/02* (2013.01); *G01N 2035/00326* (2013.01); *G01N 2035/0477* (2013.01)

(58) Field of Classification Search
None
See application file for complete search history.

(56) References Cited

U.S. PATENT DOCUMENTS

| 3,273,727 A | 9/1966 | Rogers et al. |
|---|---|---|
| 3,653,485 A | 4/1972 | Donlon |

(Continued)

FOREIGN PATENT DOCUMENTS

| CN | 201045617 Y | 4/2008 |
|---|---|---|
| CN | 102109530 A | 6/2011 |

(Continued)

OTHER PUBLICATIONS

International Search Report dated Apr. 11, 2017, in Application No. PCT/EP2017/051534, 3 pp.

*Primary Examiner* — Kavel Singh
(74) *Attorney, Agent, or Firm* — Roche Diagnostics Operations, Inc.

(57) ABSTRACT

A transport device unit for a transport device assembled using a plurality of transport device units is presented. The transport device unit comprises a base plate module with a base plate for fixing the transport device unit to a support frame, an actuator module with a plurality of electromagnetic actuators, where the actuator module is supported by the base plate module, and a driving surface module with a driving surface element, where the driving surface element is arranged above the actuator module covering the actuators and configured to carry sample container carriers. A transport device, a system for at least partially disassembling the transport device, and a laboratory sample distribution system comprising a transport device are also presented. In addition, a laboratory automation system comprising a laboratory sample distribution system is also presented.

20 Claims, 12 Drawing Sheets

(56) References Cited

U.S. PATENT DOCUMENTS

| | | |
|---|---|---|
| 3,901,656 A | 8/1975 | Durkos et al. |
| 4,150,666 A | 4/1979 | Brush |
| 4,395,164 A | 7/1983 | Beltrop et al. |
| 4,544,068 A | 10/1985 | Cohen |
| 4,771,237 A | 9/1988 | Daley |
| 5,115,905 A * | 5/1992 | Hollinger, II ........ B65G 17/46 198/465.1 |
| 5,120,506 A | 6/1992 | Saito et al. |
| 5,180,048 A * | 1/1993 | Kawada ................ B65G 54/02 198/619 |
| 5,295,570 A | 3/1994 | Grecksch et al. |
| 5,309,049 A | 5/1994 | Kawada et al. |
| 5,523,131 A | 6/1996 | Isaacs et al. |
| 5,530,345 A | 6/1996 | Murari et al. |
| 5,636,548 A | 6/1997 | Dunn et al. |
| 5,641,054 A | 6/1997 | Mori et al. |
| 5,651,941 A | 7/1997 | Stark et al. |
| 5,720,377 A | 2/1998 | Lapeus et al. |
| 5,735,387 A | 4/1998 | Polaniec et al. |
| 5,788,929 A | 8/1998 | Nesti |
| 6,045,319 A | 4/2000 | Uchida et al. |
| 6,062,398 A | 5/2000 | Thalmayr |
| 6,141,602 A | 10/2000 | Igarashi et al. |
| 6,151,535 A | 11/2000 | Ehlers |
| 6,184,596 B1 | 2/2001 | Ohzeki |
| 6,191,507 B1 | 2/2001 | Peltier et al. |
| 6,206,176 B1 | 3/2001 | Blonigan et al. |
| 6,255,614 B1 | 7/2001 | Yamakawa et al. |
| 6,260,360 B1 | 7/2001 | Wheeler |
| 6,279,728 B1 | 8/2001 | Jung et al. |
| 6,293,750 B1 | 9/2001 | Cohen et al. |
| 6,429,016 B1 | 8/2002 | McNeil |
| 6,444,171 B1 | 9/2002 | Sakazume et al. |
| 6,571,934 B1 | 6/2003 | Thompson et al. |
| 7,028,831 B2 | 4/2006 | Veiner |
| 7,078,082 B2 | 7/2006 | Adams |
| 7,122,158 B2 | 10/2006 | Itoh |
| 7,278,532 B2 | 10/2007 | Martin |
| 7,326,565 B2 | 2/2008 | Yokoi et al. |
| 7,425,305 B2 | 9/2008 | Itoh |
| 7,428,957 B2 | 9/2008 | Schaefer |
| 7,578,383 B2 | 8/2009 | Itoh |
| 7,597,187 B2 | 10/2009 | Bausenwein et al. |
| 7,850,914 B2 | 12/2010 | Veiner et al. |
| 7,858,033 B2 | 12/2010 | Itoh |
| 7,875,254 B2 | 1/2011 | Garton et al. |
| 7,939,484 B1 | 5/2011 | Loeffler et al. |
| 8,240,460 B1 | 8/2012 | Bleau et al. |
| 8,281,888 B2 | 10/2012 | Bergmann |
| 8,502,422 B2 | 8/2013 | Lykkegaard |
| 8,697,005 B2 * | 4/2014 | Indermuhle ....... B01L 3/502715 422/400 |
| 8,796,186 B2 | 8/2014 | Shirazi |
| 8,833,544 B2 | 9/2014 | Stoeckle et al. |
| 8,973,736 B2 | 3/2015 | Johns et al. |
| 9,097,691 B2 | 8/2015 | Onizawa et al. |
| 9,187,268 B2 | 11/2015 | Denninger et al. |
| 9,211,543 B2 | 12/2015 | Ohga et al. |
| 9,239,335 B2 | 1/2016 | Heise et al. |
| 9,423,410 B2 | 8/2016 | Buehr |
| 9,423,411 B2 | 8/2016 | Riether |
| 9,567,167 B2 | 2/2017 | Sinz |
| 9,575,086 B2 | 2/2017 | Heise et al. |
| 9,593,970 B2 | 3/2017 | Sinz |
| 9,598,243 B2 | 3/2017 | Denninger et al. |
| 9,618,525 B2 | 4/2017 | Malinowski et al. |
| 9,658,241 B2 | 5/2017 | Riether et al. |
| 9,664,703 B2 | 5/2017 | Heise et al. |
| 9,772,342 B2 | 9/2017 | Riether |
| 9,791,468 B2 | 10/2017 | Riether et al. |
| 9,810,706 B2 | 11/2017 | Riether et al. |
| 9,902,572 B2 | 2/2018 | Mahmudimanesh et al. |
| 9,939,455 B2 | 4/2018 | Schneider et al. |
| 9,952,242 B2 | 4/2018 | Riether |
| 9,969,570 B2 | 5/2018 | Heise et al. |
| 9,989,547 B2 | 6/2018 | Pedain |
| 10,288,634 B2 | 5/2019 | Kaeppeli |
| 2002/0009391 A1 | 1/2002 | Marquiss et al. |
| 2003/0092185 A1 | 5/2003 | Qureshi et al. |
| 2004/0050836 A1 | 3/2004 | Nesbitt et al. |
| 2004/0084531 A1 | 5/2004 | Itoh |
| 2005/0061622 A1 | 3/2005 | Martin |
| 2005/0109580 A1 | 5/2005 | Thompson |
| 2005/0194333 A1 | 9/2005 | Veiner et al. |
| 2005/0196320 A1 | 9/2005 | Veiner et al. |
| 2005/0226770 A1 | 10/2005 | Allen et al. |
| 2005/0242963 A1 | 11/2005 | Oldham et al. |
| 2005/0247790 A1 | 11/2005 | Itoh |
| 2005/0260101 A1 | 11/2005 | Nauck et al. |
| 2005/0271555 A1 | 12/2005 | Itoh |
| 2006/0000296 A1 | 1/2006 | Salter |
| 2006/0047303 A1 | 3/2006 | Ortiz et al. |
| 2006/0219524 A1 | 10/2006 | Kelly et al. |
| 2007/0116611 A1 | 5/2007 | DeMarco |
| 2007/0210090 A1 | 9/2007 | Sixt et al. |
| 2007/0248496 A1 | 10/2007 | Bondioli et al. |
| 2007/0276558 A1 | 11/2007 | Kim |
| 2008/0012511 A1 | 1/2008 | Ono |
| 2008/0029368 A1 | 2/2008 | Komori |
| 2008/0056328 A1 | 3/2008 | Rund et al. |
| 2008/0131961 A1 | 6/2008 | Crees et al. |
| 2009/0004732 A1 | 1/2009 | LaBarre et al. |
| 2009/0022625 A1 | 1/2009 | Lee et al. |
| 2009/0081771 A1 | 3/2009 | Breidford et al. |
| 2009/0128139 A1 | 5/2009 | Drenth et al. |
| 2009/0142844 A1 | 6/2009 | Le Comte |
| 2009/0180931 A1 | 7/2009 | Silbert et al. |
| 2009/0322486 A1 | 12/2009 | Gerstel |
| 2010/0000250 A1 | 1/2010 | Sixt |
| 2010/0152895 A1 | 6/2010 | Dai |
| 2010/0175943 A1 | 7/2010 | Bergmann |
| 2010/0186618 A1 | 7/2010 | King et al. |
| 2010/0255529 A1 | 10/2010 | Cocola et al. |
| 2010/0300831 A1 | 12/2010 | Pedrazzini |
| 2010/0312379 A1 | 12/2010 | Pedrazzini |
| 2011/0050213 A1 | 3/2011 | Furukawa |
| 2011/0124038 A1 | 5/2011 | Bishop et al. |
| 2011/0172128 A1 | 7/2011 | Davies et al. |
| 2011/0186406 A1 | 8/2011 | Kraus et al. |
| 2011/0287447 A1 | 11/2011 | Norderhaug et al. |
| 2012/0037696 A1 | 2/2012 | Lavi |
| 2012/0129673 A1 | 5/2012 | Fukugaki et al. |
| 2012/0178170 A1 | 7/2012 | Van Praet |
| 2012/0211645 A1 | 8/2012 | Tullo et al. |
| 2012/0275885 A1 | 11/2012 | Furrer et al. |
| 2012/0282683 A1 | 11/2012 | Mototsu |
| 2012/0295358 A1 * | 11/2012 | Ariff ..................... B65G 15/58 436/47 |
| 2012/0310401 A1 | 12/2012 | Shah |
| 2013/0069449 A1 | 3/2013 | Pharand et al. |
| 2013/0153677 A1 | 6/2013 | Leen et al. |
| 2013/0180824 A1 | 7/2013 | Kleinikkink et al. |
| 2013/0263622 A1 | 10/2013 | Mullen et al. |
| 2013/0322992 A1 | 12/2013 | Pedrazzini |
| 2014/0170023 A1 | 6/2014 | Saito et al. |
| 2014/0234949 A1 | 8/2014 | Wasson et al. |
| 2015/0014125 A1 | 1/2015 | Hecht |
| 2015/0166265 A1 | 6/2015 | Pollack et al. |
| 2015/0241457 A1 | 8/2015 | Miller |
| 2015/0273468 A1 | 10/2015 | Croquette et al. |
| 2015/0273691 A1 | 10/2015 | Pollack |
| 2015/0276775 A1 | 10/2015 | Mellars et al. |
| 2015/0276782 A1 | 10/2015 | Riether |
| 2016/0003859 A1 | 1/2016 | Wenczel et al. |
| 2016/0025756 A1 | 1/2016 | Pollack et al. |
| 2016/0054341 A1 | 2/2016 | Edelmann |
| 2016/0229565 A1 | 8/2016 | Margner |
| 2016/0274137 A1 | 9/2016 | Baer |
| 2016/0282378 A1 | 9/2016 | Malinowski et al. |
| 2016/0341750 A1 | 11/2016 | Sinz et al. |
| 2016/0341751 A1 | 11/2016 | Huber et al. |
| 2017/0059599 A1 | 3/2017 | Riether |
| 2017/0097372 A1 | 4/2017 | Heise et al. |
| 2017/0101277 A1 | 4/2017 | Malinowski |

(56) References Cited

U.S. PATENT DOCUMENTS

| | | |
|---|---|---|
| 2017/0108522 A1 | 4/2017 | Baer |
| 2017/0131307 A1 | 5/2017 | Pedain |
| 2017/0131310 A1 | 5/2017 | Volz et al. |
| 2017/0138971 A1 | 5/2017 | Heise et al. |
| 2017/0168079 A1 | 6/2017 | Sinz |
| 2017/0174448 A1 | 6/2017 | Sinz |
| 2017/0184622 A1 | 6/2017 | Sinz et al. |
| 2017/0248623 A1 | 8/2017 | Kaeppeli et al. |
| 2017/0248624 A1 | 8/2017 | Kaeppeli et al. |
| 2017/0363608 A1 | 12/2017 | Sinz |
| 2018/0067141 A1 | 3/2018 | Mahmudimanesh et al. |
| 2018/0074087 A1 | 3/2018 | Heise et al. |
| 2018/0106821 A1 | 4/2018 | Vollenweider et al. |
| 2018/0128848 A1 | 5/2018 | Schneider et al. |
| 2018/0156835 A1 | 6/2018 | Hassan |
| 2018/0188280 A1 | 7/2018 | Malinowski |
| 2018/0210000 A1 | 7/2018 | van Mierlo |
| 2018/0210001 A1 | 7/2018 | Reza |
| 2018/0217174 A1 | 8/2018 | Malinowski |
| 2018/0217176 A1 | 8/2018 | Sinz et al. |
| 2018/0224476 A1 | 8/2018 | Birrer et al. |
| 2018/0340951 A1 | 11/2018 | Kaeppell |
| 2018/0340952 A1 | 11/2018 | Kaeppeli et al. |
| 2018/0348244 A1 | 12/2018 | Ren |
| 2019/0018027 A1 | 1/2019 | Hoehnel |
| 2019/0076845 A1 | 3/2019 | Huber et al. |
| 2019/0076846 A1 | 3/2019 | Durco et al. |
| 2019/0086433 A1 | 3/2019 | Hermann et al. |
| 2019/0094251 A1 | 3/2019 | Malinowski |
| 2019/0094252 A1 | 3/2019 | Waser et al. |
| 2019/0101468 A1 | 4/2019 | Haldar |
| 2019/0285660 A1 | 9/2019 | Kopp et al. |

FOREIGN PATENT DOCUMENTS

| | | |
|---|---|---|
| DE | 3909786 A1 | 9/1990 |
| DE | 102012000665 A1 | 8/2012 |
| DE | 102011090044 A1 | 7/2013 |
| EP | 0601213 A1 | 10/1992 |
| EP | 0775650 A1 | 5/1997 |
| EP | 0916406 A2 | 5/1999 |
| EP | 1122194 A1 | 8/2001 |
| EP | 1524525 A1 | 4/2005 |
| EP | 2119643 A1 | 11/2009 |
| EP | 2148117 A1 | 1/2010 |
| EP | 2327646 A1 | 6/2011 |
| EP | 2447701 A2 | 5/2012 |
| EP | 2500871 A1 | 9/2012 |
| EP | 2502675 B1 | 2/2014 |
| EP | 2887071 A1 | 6/2015 |
| GB | 2165515 A | 4/1986 |
| JP | S56-147209 A | 11/1981 |
| JP | 60-223481 A | 11/1985 |
| JP | 61-081323 A | 4/1986 |
| JP | S61-069604 A | 4/1986 |
| JP | S61-094925 A | 5/1986 |
| JP | S61-174031 A | 8/1986 |
| JP | S61-217434 A | 9/1986 |
| JP | S62-100161 A | 5/1987 |
| JP | S63-31918 A | 2/1988 |
| JP | S63-48169 A | 2/1988 |
| JP | S63-82433 U | 5/1988 |
| JP | S63-290101 A | 11/1988 |
| JP | 1148966 A | 6/1989 |
| JP | H01-266860 A | 10/1989 |
| JP | H02-87903 A | 3/1990 |
| JP | 03-112393 A | 5/1991 |
| JP | 03-192013 A | 8/1991 |
| JP | H03-38704 Y2 | 8/1991 |
| JP | H04-127063 A | 4/1992 |
| JP | H05-69350 A | 3/1993 |
| JP | H05-142232 A | 6/1993 |
| JP | H05-180847 A | 7/1993 |
| JP | 06-26808 A | 2/1994 |
| JP | H06-148198 A | 5/1994 |
| JP | 06-156730 A | 6/1994 |
| JP | 06-211306 A | 8/1994 |
| JP | 07-228345 A | 8/1995 |
| JP | 07-236838 A | 9/1995 |
| JP | H07-301637 A | 11/1995 |
| JP | H09-17848 A | 1/1997 |
| JP | H11-083865 A | 3/1999 |
| JP | H11-264828 A | 9/1999 |
| JP | H11-304812 A | 11/1999 |
| JP | H11-326336 A | 11/1999 |
| JP | 2000-105243 A | 4/2000 |
| JP | 2000-105246 A | 4/2000 |
| JP | 2001-37201 A | 2/2001 |
| JP | 2001-124786 A | 5/2001 |
| JP | 2001-240245 A | 9/2001 |
| JP | 2005-001055 A | 1/2005 |
| JP | 2005-249740 A | 9/2005 |
| JP | 2006-106008 A | 4/2006 |
| JP | 2007-309675 A | 11/2007 |
| JP | 2007-314262 A | 12/2007 |
| JP | 2007-322289 A | 12/2007 |
| JP | 2009-036643 A | 2/2009 |
| JP | 2009-062188 A | 3/2009 |
| JP | 2009-145188 A | 7/2009 |
| JP | 2009-300402 A | 12/2009 |
| JP | 2010-243310 A | 10/2010 |
| JP | 2010-271204 A | 12/2010 |
| JP | 2013-172009 A | 2/2013 |
| JP | 2013-190400 A | 9/2013 |
| SU | 685591 A1 | 9/1979 |
| WO | 1996/036437 A1 | 11/1996 |
| WO | 2003/042048 A3 | 5/2003 |
| WO | 2007/024540 A1 | 3/2007 |
| WO | 2008/133708 A1 | 11/2008 |
| WO | 2009/002358 A1 | 12/2008 |
| WO | 2010/042722 A1 | 4/2010 |
| WO | 2012/170636 A1 | 7/2010 |
| WO | 2010/087303 A1 | 8/2010 |
| WO | 2010/129715 A1 | 11/2010 |
| WO | 201/2158520 A1 | 11/2012 |
| WO | 2012/158541 A1 | 11/2012 |
| WO | 2013/152089 A1 | 10/2013 |
| WO | 2013/169778 A1 | 11/2013 |
| WO | 2013/177163 A1 | 11/2013 |
| WO | 2014/059134 A1 | 4/2014 |
| WO | 2014/071214 A1 | 5/2014 |
| WO | 2015/033992 A1 | 3/2015 |
| WO | 2015/104263 A2 | 7/2015 |

* cited by examiner

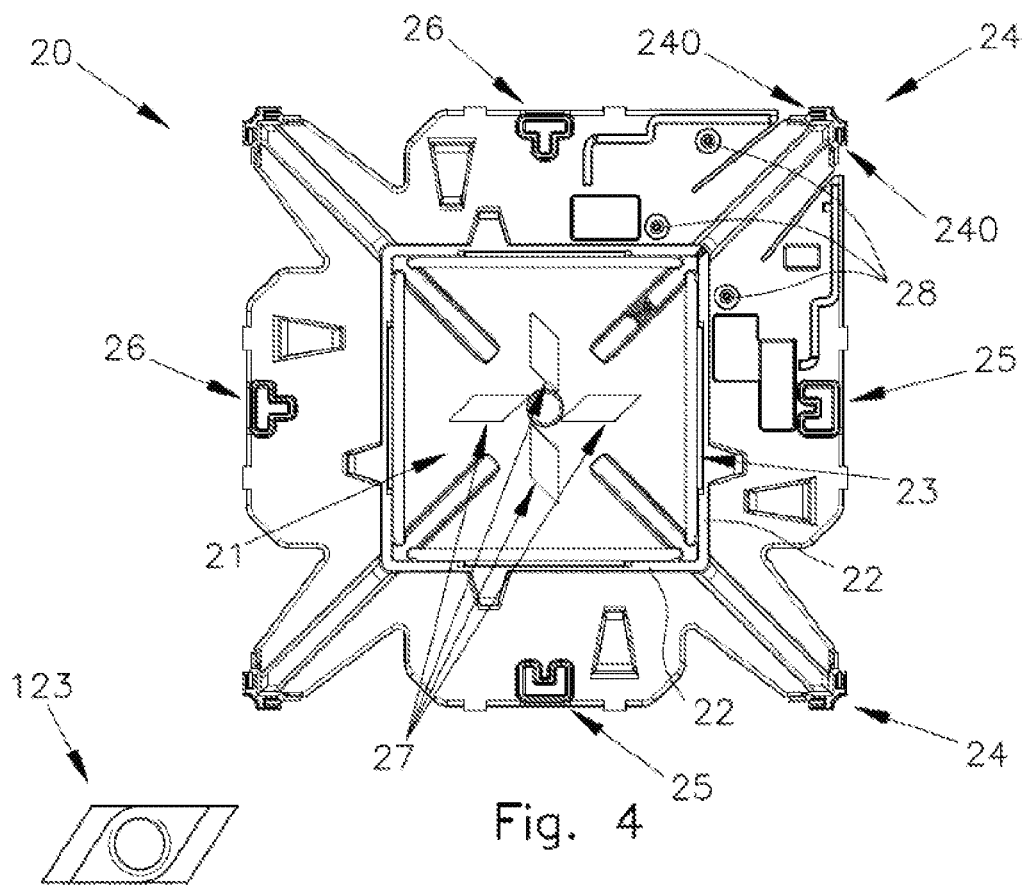
Fig. 4
Fig. 5
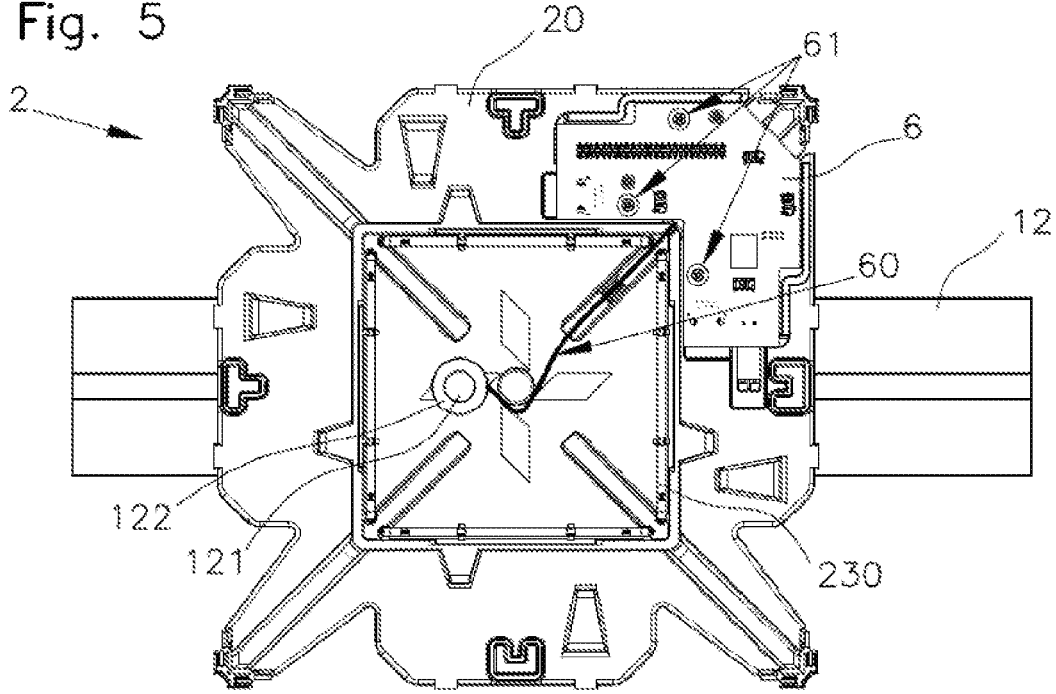
Fig. 6

TRANSPORT DEVICE UNIT FOR A LABORATORY SAMPLE DISTRIBUTION SYSTEM

CROSS-REFERENCE TO RELATED APPLICATIONS

This application is a continuation of PCT/EP2017/051534 filed Jan. 25, 2017, which is based on and claims priority to EP 16157587.3 filed Feb. 26, 2016, which are hereby incorporated by reference.

BACKGROUND

The present disclosure generally relates to a transport device unit for a transport device assembled using a plurality of transport device units and, in particular, to a transport device, a system for at least partially disassembling the transport device, and a laboratory sample distribution system comprising a transport device as well as an automation system comprising a laboratory sample distribution system.

A laboratory automation system comprises a plurality of pre-analytical, analytical and/or post-analytical stations, in which samples, for example blood, saliva, swab and other specimens taken from the human body, are processed. It is generally known to provide various containers, such as test tubes or vials, containing the samples. The test tubes are also referred to as sample tubes. In the context of the application, containers such as test tubes or vials for containing a sample are referred to as sample containers.

There is a need for a transport device comprising a plurality of electro-magnetic actuators stationary arranged below a driving surface, in which the transport device is flexible in design and can be adapted to a large number of different requirements

SUMMARY

According to the present disclosure, a transport device unit for a transport device assembled using a plurality of transport device units is presented. The transport device unit can comprise a base plate module with a base plate for fixing the transport device unit to a support frame, an actuator module with a plurality of electro-magnetic actuators, wherein the actuator module is supported by the base plate module, and a driving surface module with a driving surface element. The driving surface element can be arranged above the actuator module covering the actuators and configured to carry sample container carriers. The base plate module and the actuator module can have cooperating male and female coupling elements. The male and female coupling elements can assume shapes and/or can be arranged for a mechanical coding not having rotational symmetry for ensuring a correct alignment of the base plate module and the actuator module.

Accordingly, it is a feature of the embodiments of the present disclosure to provide a transport device comprising a plurality of electro-magnetic actuators stationary arranged below a driving surface, in which the transport device is flexible in design and can be adapted to a large number of different requirements. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which:

FIG. 4 illustrates a top view of a base plate of a base plate module of the transport device unit of FIG. 2 according to an embodiment of the present disclosure.

FIG. 5 illustrates a top view of a rhombic slot nut according to an embodiment of the present disclosure.

FIG. 6 illustrates a top view of a base plate module of the transport device unit of FIG. 2 according to an embodiment of the present disclosure.

DETAILED DESCRIPTION

Figure 1:
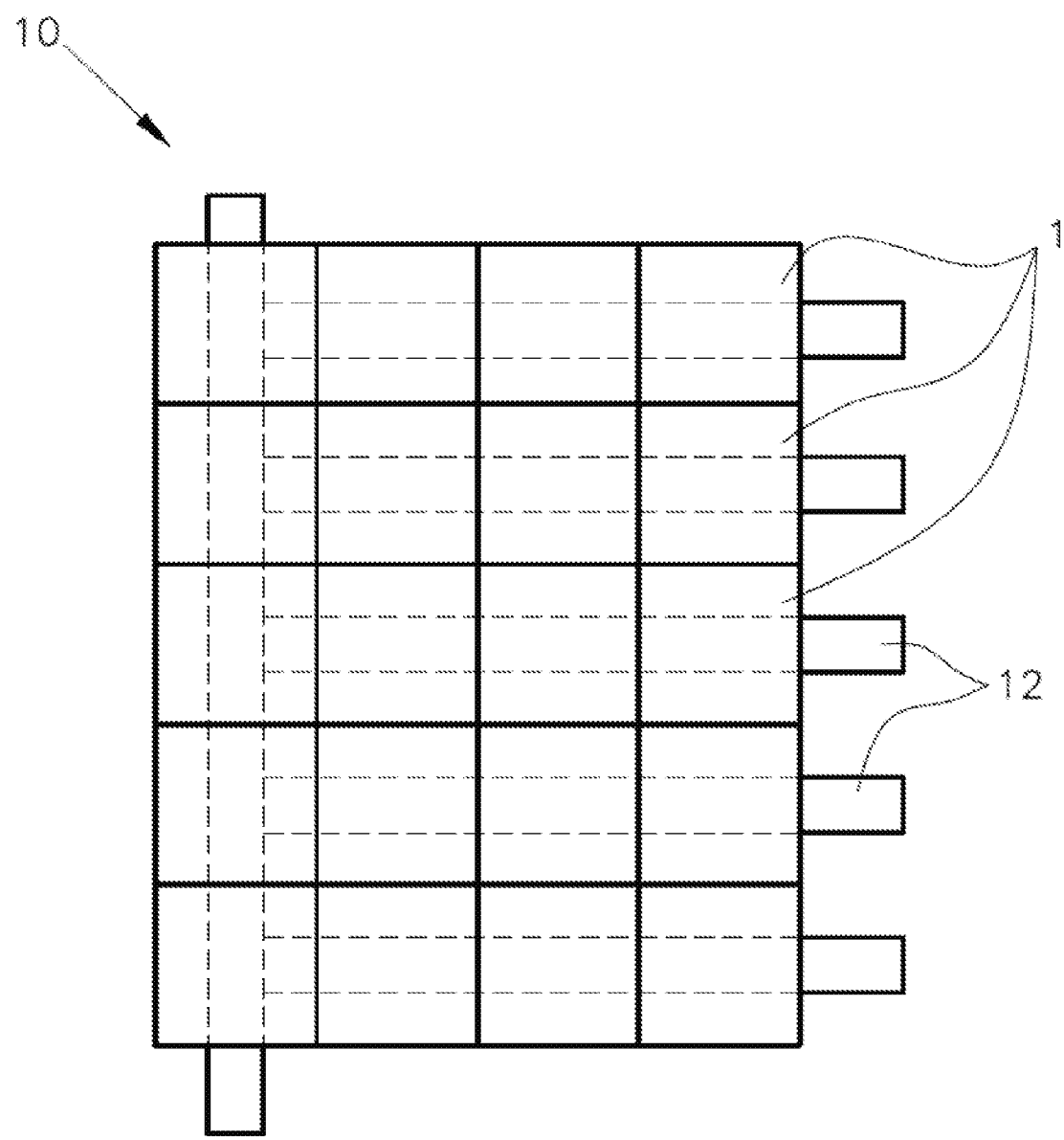
FIG. 1 illustrates a top view of a transport device build from several transport device units according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A transport device unit for a transport device assembled using a plurality of transport device units is presented. The transport device unit can comprise a base plate module with a base plate for fixing the transport device unit to a support frame, an actuator module with a plurality of electromagnetic actuators, wherein actuator module can be supported by the base plate module, and a driving surface module with a driving surface element. The driving surface element can be arranged above the actuator module covering the actuators and can be configured to carry sample container carriers.

The base plate module and the actuator module can have cooperating male and female coupling elements. The male and female coupling elements can assume shapes and/or can be arranged for a mechanical coding not having rotational symmetry for ensuring a correct alignment of the base plate module and the actuator module. A suitable keying system can be chosen by the person skilled in the art.

Each unit can be an independent, fully functional element. Hence, a transport device can be assembled using an arbitrary number of units arranged in an arbitrary configuration.

The driving surface module can comprise a driving surface element configured to carry sample container carriers. In one embodiment, sample container carriers can have rollers for a movement across the driving surface element or a driving surface pieced together from driving surface elements of neighboring transport device units. In some embodiments, the sample container carriers can be moved slidingly across the driving surface element. For this purpose, the driving surface element can be made from or coated with a material having a low sliding friction coefficient such as, for example, in combination with a material used at a sliding surface of the sample container carrier, as well as high abrasion resistance. The modules of the units can be detachably coupled to each other allowing for an individual mounting and/or an individual replacement, when required. For an assembly of a transport device, initially, a basic framework can be provided by fixing the base plate modules to a support frame. When fixing the base plate modules to the support frame, the base plates can be aligned in height. The size of each unit can be chosen such that a single person may be sufficient for a handling during assembly. In one embodiment, units of different sizes and basic shapes can be provided which can be assembled to a transport device.

In some embodiments, the transport device unit can have a tessellating basic shape such as, for example, a regular polygonal basic shape. Hence, an arbitrary number of transport device units identical in design can be assembled to a transport device.

In one embodiment, the transport device unit and its modules can have a regular polygonal basic shape with at least three sides and at least three corners, wherein male or female coupling elements can be provided at each side of the base plate module and the actuator module, respectively. In one embodiment, the shapes of all coupling elements can differ. Alternatively, or in addition, coupling elements provided at different sides can differ in position with respect to the associated side.

In one embodiment, the driving surface module can be detachably mounted to the base plate module. When mounting the driving surface module detachably, the driving surface module can be removed to allow access to the actuator module, for example, in order to replace a malfunctioning or defect actuator. When mounting the driving surface module to the base plate module and not to the actuator module, the driving surface module can be positioned more accurate. In one embodiment, the driving surface module can comprise a sensor board arranged at a bottom side of the driving surface element. The sensor board can at least form part of a device for sensing a presence or position of a sample container carrier moved across the upper side of the driving surface element. In one embodiment, the driving surface element can be transparent to IR light, wherein the sensor board can be equipped with multiple IR based reflection light barriers arranged in a grid, and the sample container carriers can be configured to reflect IR radiation emitted by the light barriers. When mounting the driving surface module to the base plate module, a precise positioning of the driving surface module in relation to the base plate module can be achieved. A misalignment between the actuator module and the base plate module may be acceptable within tolerances. Hence, the technical requirements for mounting the actuator module to the base plate module can be less restrictive than for mounting the driving surface module.

The base plate module can be used for fixing the transport device unit to a support frame. For this purpose, in one embodiment, the base plate of the base plate module can have at least one aperture configured to allow a slot nut to be passed through for mounting the transport device unit to a support bar of the support frame by the slot nut. The apertures can allow an insertion of slot nuts into grooves of a support bar after placing the base plate module on the support bar. In one embodiment, rhombic apertures for rhombic slot nuts can be provided. In order to allow a mounting of the transport device unit in more than one orientation to a support bar and/or to support bars extending in different directions, in one embodiment, at least two apertures arranged at an angle of about 90° can be provided.

The electro-magnetic actuators of the actuator module can be configured to move a sample container carrier on top of the driving surface in at least two different directions using magnetic forces. It is well known to provide a control device, which can be configured to control the movement of the container carriers on top of driving surface by driving the electro-magnetic actuators. A wiring board can be provided at each transport device unit for connecting the transport device unit with the control device and for communicating the actuator module with the control device.

In one embodiment, the wiring board can be mounted to the base plate, wherein in some embodiments, the wiring board can have a board-to-board connector for an electrical and mechanical coupling with an actuator module wiring board of the actuator module. When mounting the wiring board to the base plate, a wiring of the transport device can be completed prior to mounting the actuator module. At this stage of the assembly of the transport device, the wiring boards provided at the base plate modules can be easy to access. In order to avoid a wiring between the wiring board and the actuator module wiring board, the board-to-board connector can be provided.

In some embodiments, the wiring board and the actuator module wiring board can be provided with cooperating centering elements to ensure a correct alignment of the board-to-board connector and contact pins protruding from the actuator module wiring board. In this case, to avoid an overdetermined mechanical system, the wiring board can be float-mounted to the base plate. Hence, the wiring board can be moveable within limits in respect to the base plate and, thus, can be moved for aligning the wiring board with the actuator wiring board arranged fixed in position at the actuator module when mounting the actuator module to the base plate module.

The unit, in some embodiments, can comprise a fan for a cooling. In this case, in one embodiment, the base plate can be provided with a recess for accommodating the fan, wherein at least one filter element can be detachably mounted to insides of walls surrounding the recess.

The fan, in one embodiment, can be mounted to the base plate module. In other embodiments, the fan can be mounted to a bottom side of the actuator module and placed in the recess upon mounting the actuator module to the base plate module.

Commercially available fans typically have a circular basic shape. A recess for accommodating the fan, in some embodiments, can have a rectangular such as, for example, a square, basic shape. In this case, in one embodiment, four separate filter elements can be detachably mounted to insides of walls surrounding the recess. Each filter element can be replaced individually. The filter elements can, in one embodiment, be mounted using screws or similar elements for a detachable connection. In alternative, snap-fit elements can be provided allowing for a quick and easy attaching or detaching of filter elements. In this case, in one embodiment, the snap-fit elements can be destroyed upon detachment of the filter elements in order to avoid a re-use thereof. In other embodiments, the filter elements can be detachable without destruction of the snap-fit elements.

In one embodiment, the actuator module can be provided with stands protruding from a bottom surface and serving as male coupling elements for coupling the actuator module to the base plate module. The stands can be used for placing the actuator module on a surface when not mounted to the base plate module, for example, during transport, assembly or storage.

Each unit can comprise a plurality of actuators. For an efficient manufacturing of the actuator modules, in one embodiment, the actuator module can have an actuator module wiring board having sockets and a magnetically conductive structure and the actuators can have contact pins, wherein the actuators can be mounted to the magnetically conductive structure such that the contact pins can be electrically and mechanically connected with the sockets. In other words, the actuators can be positioned upon mounting at the magnetically conductive structure. For allowing the contact pins to pass through the structure into the sockets, in some embodiments, a magnetically conductive grid structure can be provided. The magnetically conductive structure can have mounting positions for the actuators, wherein, for example, the magnetically conductive structure can have bearing pins configured to receive actuators having a core. The mounting positions, in one embodiment, can coincide with nodes of the grid structure.

A transport device comprising a plurality of transport device units is presented. The modular construction of the transport device can offer a great range of set-up options. Neighboring transport device units can be coupled to each other to ensure a correct alignment and to avoid gaps in a driving surface pieced together by driving surface modules. The transport device units, for example, can be coupled at adjacent sides.

In one embodiment, the base plate modules of neighboring transport device units can be coupled and aligned at their adjacent corners by corner supports.

For an assembly of a transport device from a plurality of transport device units, initially the base plate modules can be mounted to a support frame. Next, the actuator modules can be mounted to the base plate modules. Finally, the driving surface modules can be mounted to the base plate modules. For a disassembling, the steps can be carried out in reverse order. The removal of actuator modules surrounded by further actuator modules can be challenging. Hence, for a disassembling, one can start with a removal of actuator modules arranged at outer edges of the transport device, which may not be fully surrounded by further actuator modules.

A system comprising the transport device and at least one a removal tool configured to be inserted between two actuator modules of neighboring transport device units is presented. The at least one removal tool and the actuator module can have cooperating coupling elements. The removal tool can allow a removal of actuator modules surrounded by further actuator modules without the necessity to remove all actuator modules starting from outer edges of the transport device.

A laboratory sample distribution system is presented having a transport device and a plurality of sample container carriers. The sample container carriers can each comprise at least one magnetically active device such as, for example, at least one permanent magnet, and configured to carry a sample container containing a sample. The magnetic actuators of the transport device units of the transport device can be suitably driven for generating a magnetic field such that a driving force can be applied to each of the sample container carriers for transporting the sample container carriers on the surface pieced together of driving surface modules of the units. The distribution system in addition, in one embodiment, can comprise additional conveyor devices for moving a sample container carrier along a defined path.

A laboratory automation system with a plurality of pre-analytical, analytical and/or post-analytical stations, and with a distribution system having a transport device and number of sample container carriers is also presented.

Referring initially to FIG. 1, FIG. 1 schematically shows a top view of an embodiment of a transport device 10 build from several, in the embodiment shown, twenty transport device units 1. The transport device units 1 can be fixed to a support frame comprising support bars 12. Each of the transport device units 1 shown can have a square basic shape allowing building of transport devices 10 of various designs by adding additional transport device units 1 at either side of already existing units 1 and/or removing transport device units 1 from the device 10 shown in FIG. 1. In other embodiments, the transport device units can have a different basic shape, for example, a triangular basic shape or a hexagonal basic shape. In some embodiments, all transport device units 1 can have the same basic shape, wherein the shape can be a tessellating shape. However, in specific embodiments, a transport device can be composed of transport device units 1 having different basic shapes.

Figure 2:
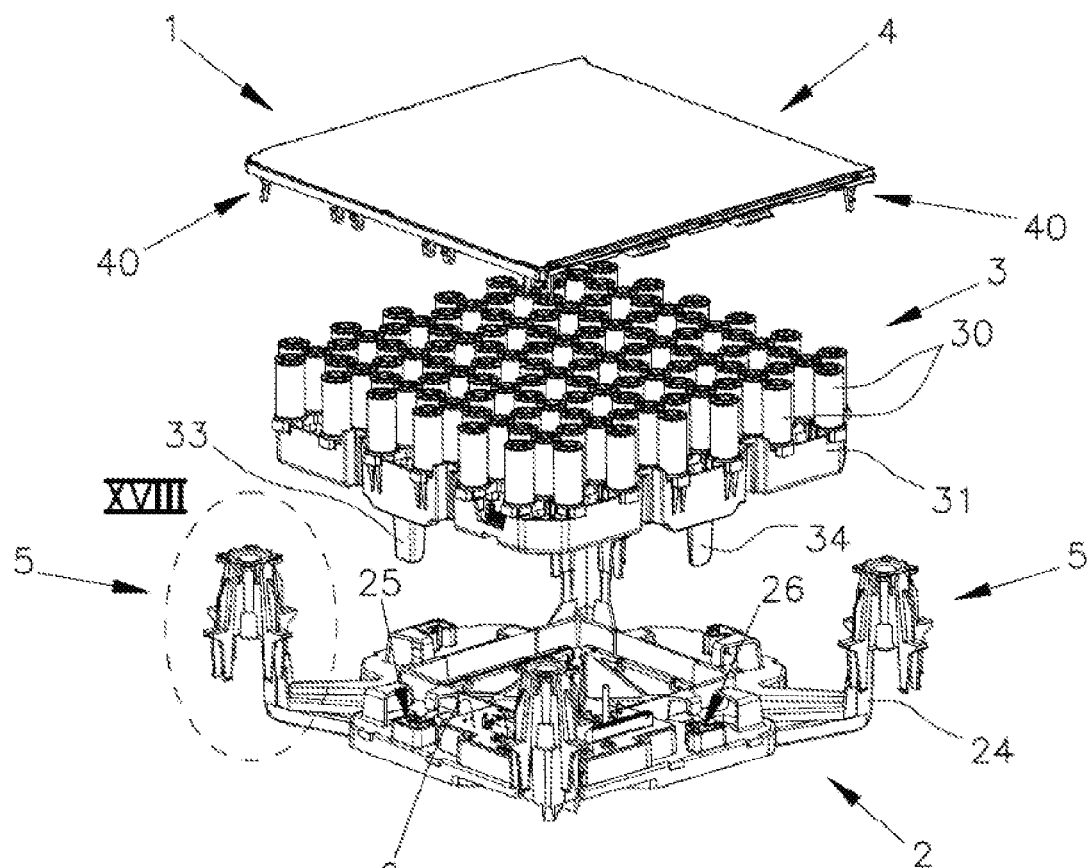
FIG. 2 illustrates an exploded view of a transport device unit according to an embodiment of the present disclosure.
Figure 3:
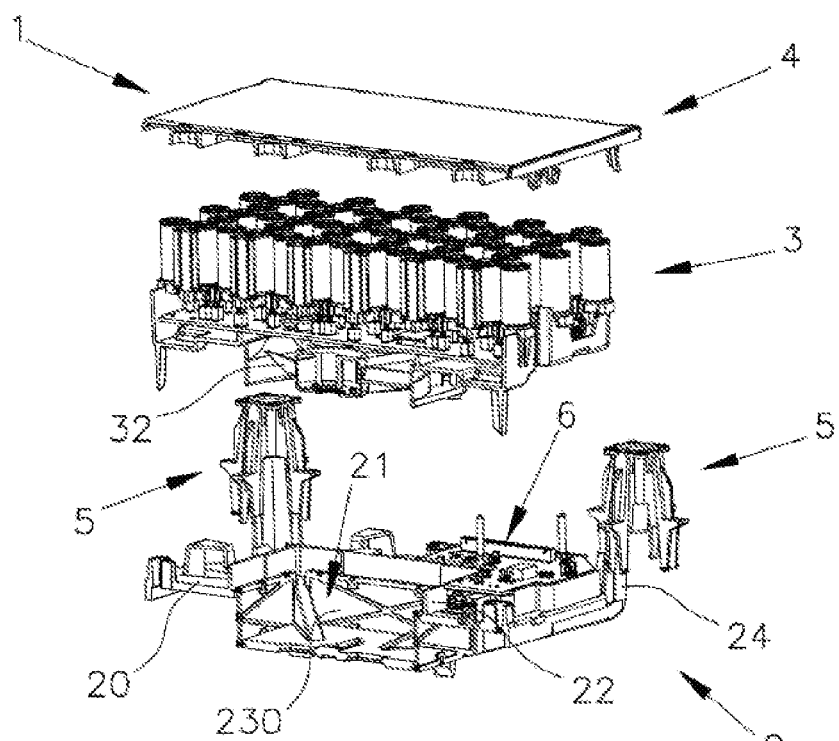
FIG. 3 illustrates a sectional exploded view of the transport device unit of FIG. 2 according to an embodiment of the present disclosure.

FIG. 2 shows a transport device unit 1 for building a transport device 10 of FIG. 1 in an exploded view. FIG. 3 shows the unit 1 of FIG. 2 in an exploded sectional view. The transport device unit 1 can comprise three modules, namely a base plate module 2 for fixing the transport device unit 1 to the support frame, an actuator module 3 with a plurality of electro-magnetic actuators 30 mounted to a carrier element 31, and a driving surface module 4. Adjacent transport device units 1 can be connected by corner supports 5.

The base plate module 2 shown can comprise a base plate 20 having a substantially square basic shape with four sides and four corners. In the center area of the base plate 20, a recess 21 surrounded by walls 22 can be provided for accommodating a fan 32 mounted at the actuator module 3 and protruding from a bottom side of the carrier element 31. At the inside of the walls 22, filter elements 230 can be mounted.

A wiring board 6 can be mounted to the base plate 20 at one corner region thereof. In the embodiment shown, the wiring board 6 can have a substantially L-shaped basic shape and can be arranged directly adjacent to the recess 21.

Neighboring base plate modules 2 can be coupled to each other. For this purpose, in the embodiment shown, at each corner of the base plate module 2, an angled connection bracket 24 extending in a vertical direction and substantially perpendicular to a surface area of the base plate 20 can be provided. Adjacent base plates 20, and thus adjacent base plate modules 2, can be connected by the corner supports 5 attached to two, three or four connection brackets 24 of the base plates 20 of neighboring transport device units 1. The driving surface module 4 can be coupled to a top end of the corner supports 5 by connecting structures 40 provided at each of the four corners of the driving surface module 4.

The actuator module 3 can be supported by the base plate module 2. For this purpose, the base plate module 2 and the actuator module 3 can have cooperating male and female coupling elements. In the embodiment shown, the base plate 20 can have four receiving openings 25, 26 configured to receive four stands 33, 34 provided at the actuator module 3.

For assembling the transport device 10 shown in FIG. 1 from a plurality of transport device units 1, at first a plurality of base plate modules 2 can be mounted to the support bars 12 (see FIG. 2), wherein adjacent base plate modules 2 can be aligned and connected to each other by the corner supports 5. Next, a wiring of the transport device units 1 can be completed. After the wiring is completed, the actuator modules 3 can be mounted to the base plate modules 2, wherein the stands 33, 34 of the actuator module 3 can be inserted into the receiving openings 25, 26 of the base plate 20. Finally, the driving surface module 4 can be mounted to the base plate module 2 via the corner supports 5, wherein the connecting structures 40 of the driving surface module 4 can be coupled to the corner supports 5.

FIG. 4 shows the base plate 20 of the base plate module 2 in a top view. FIG. 6 shows the base plate module 2 in a top view mounted to a support bar 12.

As can be seen in FIG. 4, close to its center, the surface area of the base plate 20 can have four rhombic apertures 27, each configured to receive a fastening bolt 121 (see FIG. 6) equipped with a washer 122 and a rhombic slot nut 123. The rhombic slot nut 123 is schematically shown in FIG. 5. The slot nut 123 can be mounted to the fastening bolt 121 and inserted from above into a groove of the support bar 12 passing through the rhombic apertures 27. This can allow for an easy mounting, wherein the fastening bolt 121 can be tightened after all base plate modules 2 of a transport device are aligned to each other.

As shown in FIG. 4, the surface area of the base plate 20 can have receiving slits 23 on the internal side of the walls 22 surrounding the recess 21. The receiving slits 23 can allow mounting of filter elements 230 (see FIGS. 6 and 7) from below, in case the support bar 12 does not hinder an access to the receiving slit 23. In case access to the receiving slit 23 from below is hindered by the support bar 12 as in the case of the receiving slits 23 on the left and the right in FIG. 6, the filter element 230 can be mounted from above.

To one corner of the base plate 20, in the orientation shown in FIGS. 4 and 5, to the upper right corner, a wiring board 6 can be mounted. The wiring board 6 can be mounted to the base plate 20 by screws 61 (see FIG. 6). For this purpose, as shown in FIG. 4, the base plate 20 can have threaded holes 28 for receiving the screws 61. As shown in FIG. 6, in the embodiment shown, an earth or ground cable 60 of the wiring board 6 can be connected to the fastening bolt 121 and the fastening bolt 121 can be used as ground for the wiring board 6.

The base plate module 2 can serve as a mounting platform for mounting the actuator module 3 and the driving surface module 4.

The actuator module 3 can be mounted to the base plate module 2 by stands 33, 34 (see FIG. 3) serving as male coupling elements to be inserted into receiving openings 25, 26 provided at the base plate 20. As best seen in FIG. 4, the receiving openings 25, 26 configured to receive the stands 33, 34 can differ in design for providing a mechanical coding or keying system not having rotational symmetry. Thereby, it may be ensured that the actuator module 3 can only be mounted in one particular orientation to the base plate module 2. In the embodiment shown, two receiving openings 25 have a substantially U-shaped design, whereas the other two receiving openings 26 have a substantially T-shaped design. Each receiving opening 25, 26 can be arranged at a center of one of the sides of the base plate 20 between two corners. In other embodiments, a keying structure can be provided by arranging at least one of the receiving openings 25, 26 and the corresponding stand 33, 34 offset from a center closer to one corner.

As explained above, the base plates 20 of adjacent transport device units 1 can be coupled and aligned using corner supports 5 (see FIG. 2) attached to the connection brackets 24 at adjacent corners of the base plates 20. In the embodiment shown, each connection bracket 24 can have two longitudinal grooves 240 at its two legs, in which the longitudinal grooves 240 can extend substantially parallel to the two adjoining sides and substantially perpendicular to a surface area of the base plate 20. A coupling element can be inserted into the grooves from above.

Figure 7:
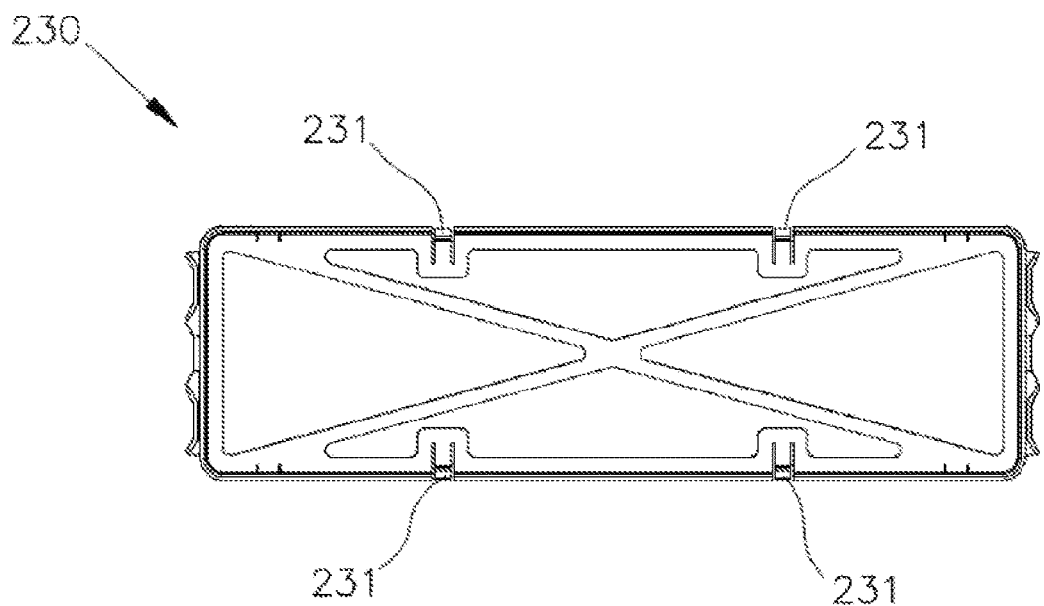
FIG. 7 illustrates a side view of a filter element used in the base plate module of FIG. 6 according to an embodiment of the present disclosure.

FIG. 7 shows a filter element 230 of the base plate module 2 of FIG. 6 in a side view. As can be seen in FIG. 7, the filter element 230 can have mirror symmetry allowing a mounting of the filter element 230 in four different orientations. The filter element 230 can have snap-fit connectors 231 for detachably securing the filter element 230 in position at the base plate 20 of the base plate module 2. If required, the filter element 230 can be removed and cleaned or replaced. In case access to the filter element 230 is possible from below, such a removal and/or replacement can be possible without disassembling the transport device unit 1.

Figure 8:
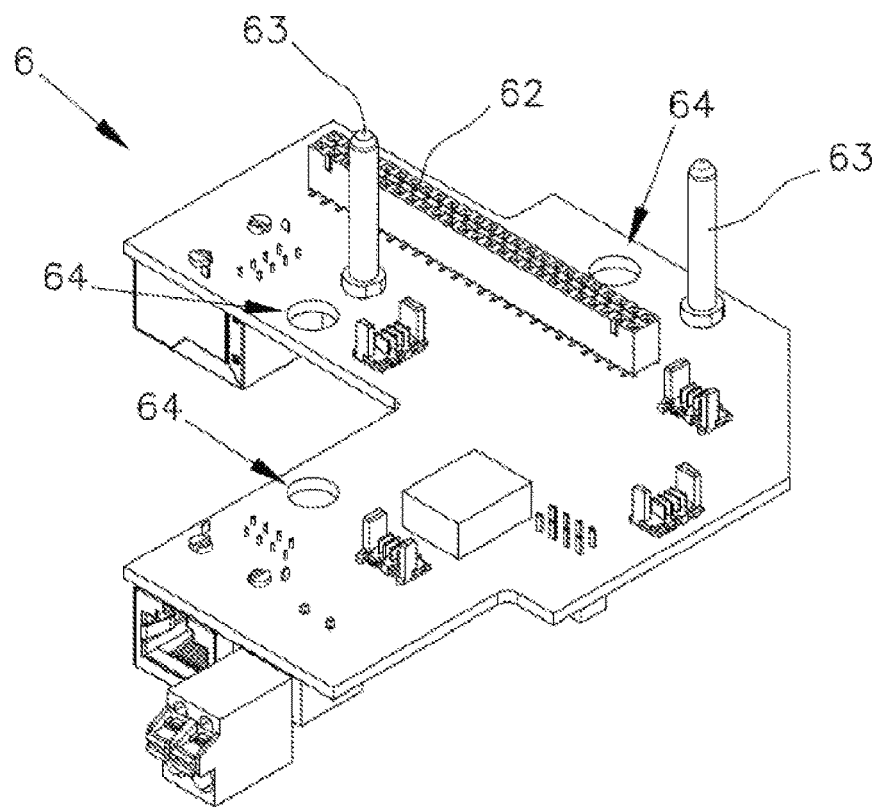
FIG. 8 illustrates a perspective view of a wiring board used in the base plate module of FIG. 6 according to an embodiment of the present disclosure.

FIG. 8 shows the wiring board 6 of the base plate module 2 of FIG. 6 in a perspective view. As can be seen in FIG. 8, the wiring board 6 can have a board-to-board connector 62 for electrically connecting the wiring board 6 and the actuator module 3 (see FIG. 2) such as, for example, for electrically connecting the wiring board 6 and an actuator module wiring board 35 (see FIG. 11). In order to ensure a correct alignment of the wiring board 6 and the actuator module 3, two centering pins 63 can be provided, which can be received in corresponding centering holes (36, see FIG.

10) at the actuator module 3. In order to avoid an overdetermined mechanical system, the wiring board 6 can be float-mounted to the base plate 20 of the base plate module 2. For this purpose, in the embodiment shown, the wiring board 6 can have through holes 64 for the fixation screws 61 (see FIG. 6), in which the through holes 64 can be larger in diameter than the fixation screws 61. Hence, the wiring board 6 can be mounted moveably within limits by the fixation screws 61 to the base plate 20.

Figure 9:
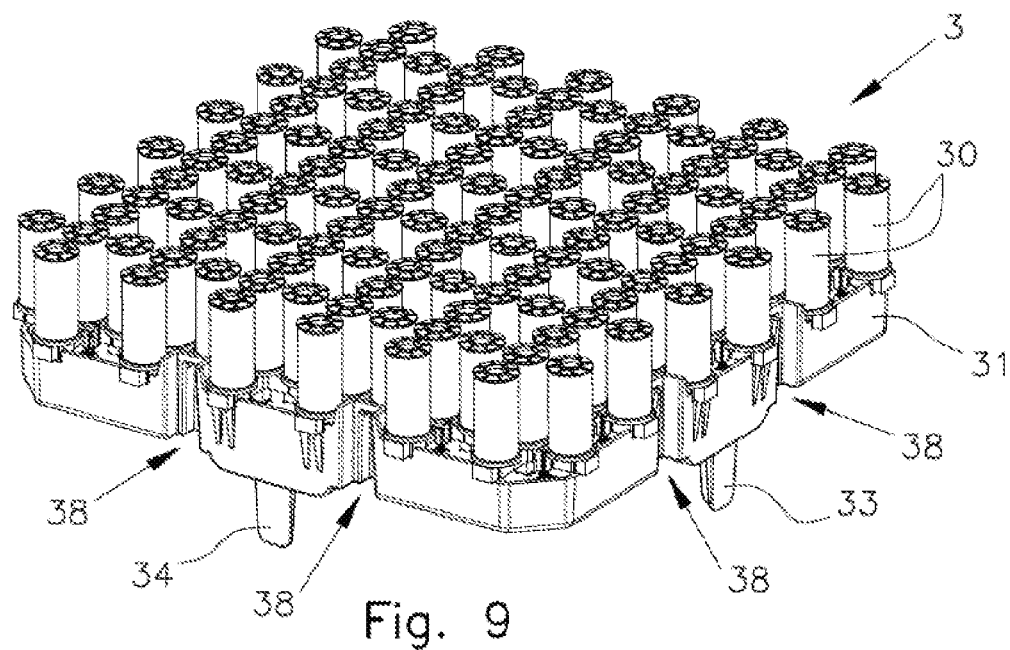
FIG. 9 illustrates a perspective view from above of an actuator module of the transport device unit of FIG. 2 according to an embodiment of the present disclosure.
Figure 10:
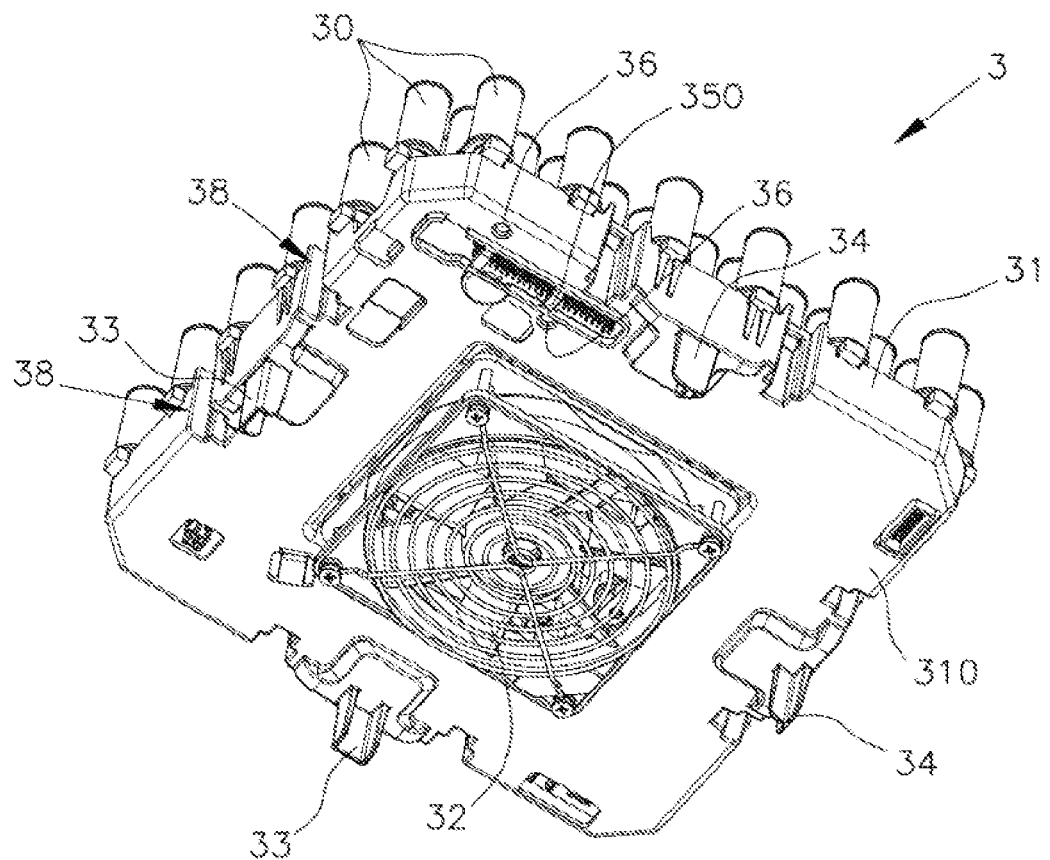
FIG. 10 illustrates a perspective view from below of the actuator module of FIG. 9 according to an embodiment of the present disclosure.
Figure 11:
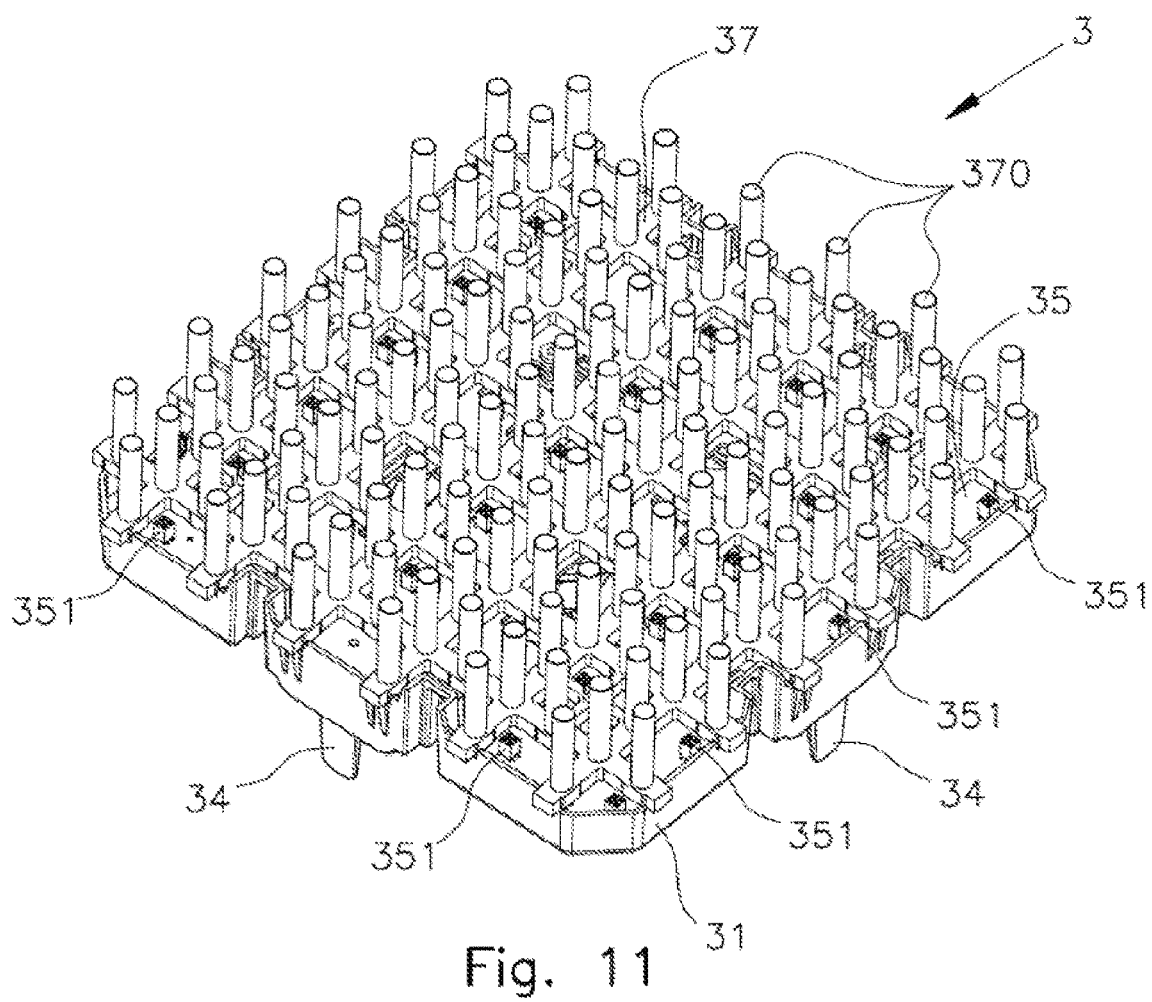
FIG. 11 illustrates a perspective view from above of the actuator module of FIG. 9 without actuators according to an embodiment of the present disclosure.
Figure 12:
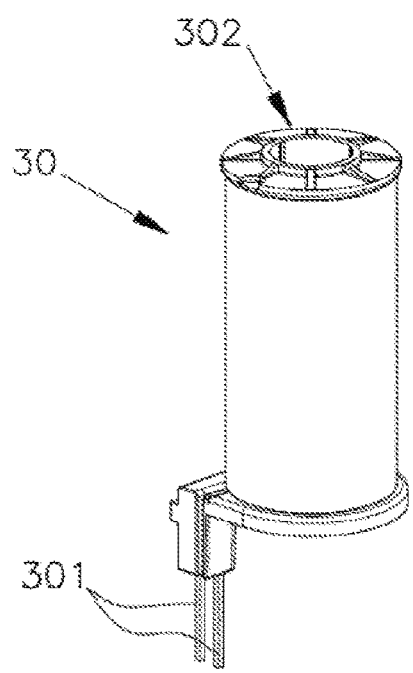
FIG. 12 illustrates a perspective view of an actuator of the actuator module of FIG. 9 according to an embodiment of the present disclosure.

FIGS. 9 and 10 show the actuator module 3 with the carrier element 31 and the actuators 30 in a perspective view from above and from below, respectively. FIG. 11 shows the actuator module 3 in a different orientation than FIG. 9 and wherein the actuators 30 are removed. FIG. 12 shows an electro-magnetic actuator 30 of the actuator module 3.

The actuator module 3 has a substantially square basic shape with four equal sides and four corners. It can be configured to be mounted to the base plate module 2 by the stands 33, 34 inserted into receiving openings 25, 26 (see FIG. 4, 6). As mentioned above, the carrier element 31 can have four stands 33, 34 configured to be inserted into four receiving openings 25, 26 of the base plate module 2 (see FIG. 2). The receiving openings 25, 26, as well as the corresponding stands 33, 34, can differ in design for providing a mechanical coding not having rotational symmetry. In the embodiment shown, two stands 33 can have a substantially U-shaped cross-section, whereas the other two stands 34 can have a substantially T-shaped cross-section. Each stand 33, 34 can be arranged at a center of one of the sides of the carrier element 31.

The actuator module 3 can comprise an actuator module wiring board 35 provided with contact pins 350 accessible via a bottom surface 310 of the carrier element 31. The contact pins 350 can be configured to connect with the board-to-board connector 62 (see FIG. 8) of the wiring board 6. In order to ensure for a correct alignment of the contact pins 350 and the board-to-board connector 62 of the wiring board 6, two centering holes 36 can be provided at the bottom surface 310 as well as at the actuator module wiring board 35. The centering holes 36 can be configured to receive the centering pins 63 of the wiring board 6 for aligning the contact pins 350 of the actuator module wiring board 35 with the board-to-board connector 62.

The actuators 30 can be electrically and mechanically connected to the actuator module wiring board 35. For this purpose, as best seen in FIG. 11, the actuator module wiring board 35 can be equipped with a plurality of sockets 351 configured to receive contact pins 301 provided at the actuators 30 (see FIG. 12). In order to facilitate a mounting of the actuators 30 to the actuator module 3, in the embodiment shown, the actuator module 3 can comprise a grid structure 37 made of a magnetically conductive material such as, for example, a metal, comprising a plurality of bearing pins 370. The bearing pins 370 can be configured to receive one actuator 30 each, wherein the actuators 30 can have corresponding cores 302.

At a bottom side of the actuator module 3, the fan 32 can be provided. The length of the stands 33, 34 can exceed the distance over which the fan 32 can protrude from the bottom surface 310 such that when placing the actuator module 3 on a planar surface, for example during transport, for storage and/or for an assembly, the distal ends of the stands 33, 34 can contact this planar surface and the fan 32 can be distanced from the planar surface. Hence, it can be possible to mount the fan 32 directly to the actuator module wiring board 35.

At each side of each stand 33, 34, a guiding groove 38 for a removal tool 8 (see FIGS. 21, 22) can be provided, as will be explained in more detail with reference to FIGS. 21 and 22 below.

Figure 13:
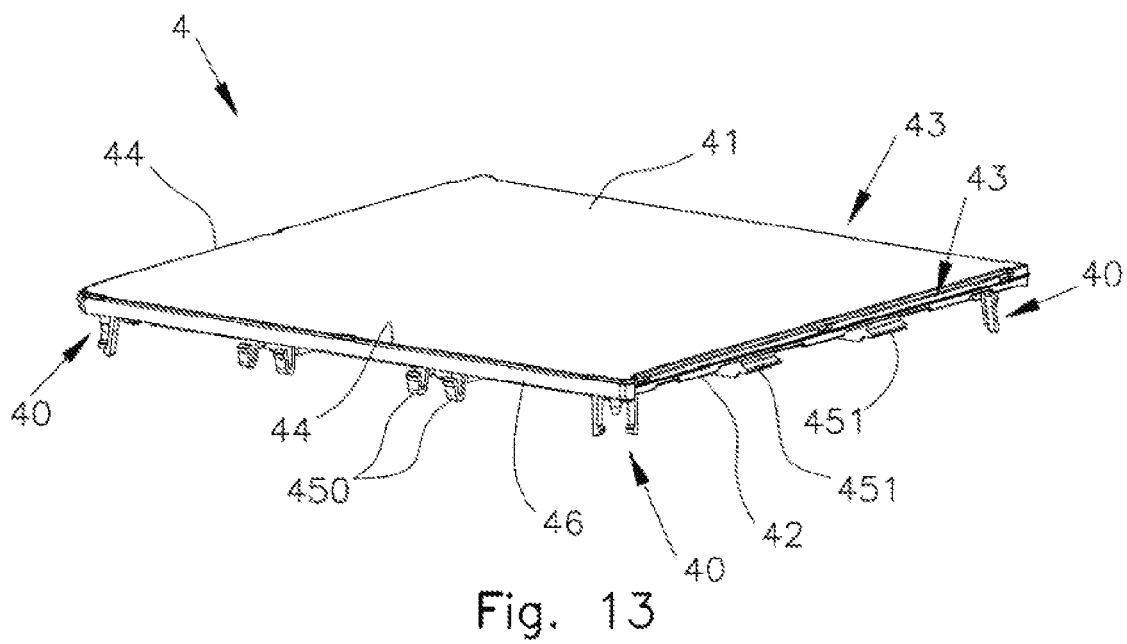
FIG. 13 illustrates a perspective view from above of a driving surface module of the transport device unit of FIG. 2 according to an embodiment of the present disclosure.
Figure 14:
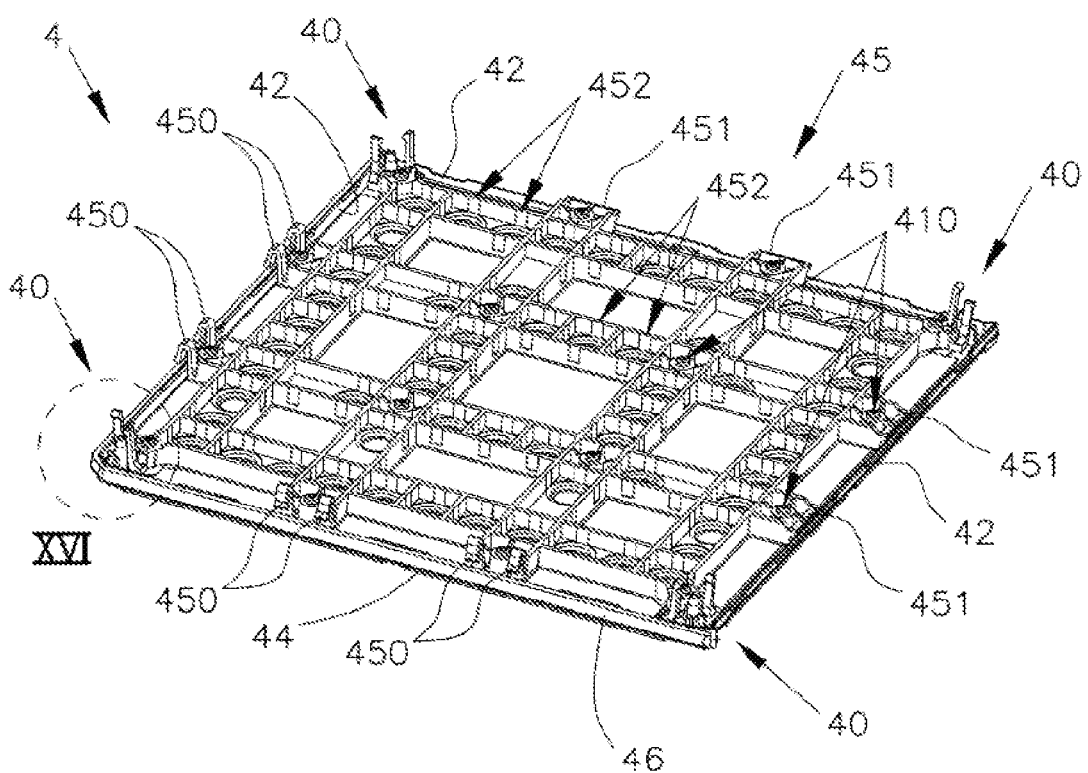
FIG. 14 illustrates a perspective view from below of the driving surface module of FIG. 13 according to an embodiment of the present disclosure.
Figure 15:
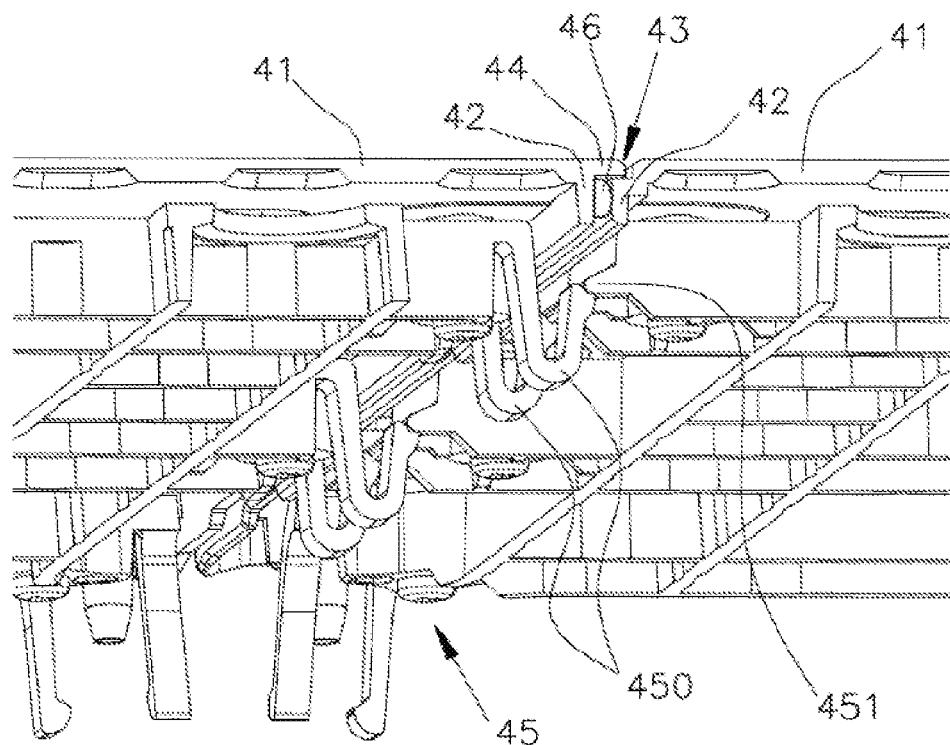
FIG. 15 illustrates a perspective view from below showing a detail of two adjacent driving surface modules of FIG. 13 according to an embodiment of the present disclosure.

FIGS. 13 and 14 show the driving surface module 4 in a perspective view from above and from below, respectively. FIG. 15 is a perspective view from below showing a detail of two adjacent driving surface modules 4 of FIG. 14.

The driving surface module 4 can have a driving surface element 41. The driving surface element 41 can be made of a material suitable for slidingly transporting sample carriers along the top surface of the driving surface element 41. The driving surface element 41 can have a substantially square basic shape with four sides of equal length and four corners.

The driving surface module 4 can be detachably supported by support elements. In the embodiment shown, the driving surface module 4 can be detachably supported by the corner supports 5 (see FIG. 2) serving as support element for the driving surface module 4. At the four corners of the driving surface module 4, connecting structures 40 can connect the driving surface module 4 via the corner supports 5 with the base plate module 2 (see FIG. 2). The driving surface module 4 can comprise a sensor board arranged at a bottom side of the driving surface element 41. Hence, the sensor board can be positioned close to the driving surface across which sample support carriers can be transported. The sensor board can at least form part of a device for sensing a presence or position of an individual sample container carrier moved across the upper side of the driving surface element 41. In one embodiment, the driving surface element 41 can be transparent to IR light, wherein the sensor board can be equipped with multiple IR based reflection light barriers arranged in a grid, and the sample container carriers can be configured to reflect IR radiation emitted by the light barriers.

When mounting the driving surface module 4 to the base plate module 2 by the corner supports 5, the driving surface module 4 can be positioned with high accuracy in relation to the base plate module 2.

At each side of the driving surface element 41, a rim 42 can be provided.

The driving surface elements 41 of adjacent transport device units 1 can overlap each other at their side regions. For this purpose, as best seen in FIGS. 14 and 15, at two adjoining sides of each driving surface module 4, a transition between the top surface of the driving surface element 41 and the rim 42 can have a stepped portion 43. At the respective opposing sides of each driving surface module 4, a transition between the top surface of the driving surface element 41 and the rim 42 can have a complementary overhang portion 44. The stepped portion 43 and the overhang portion 44 can be configured to each other such that the overhang portion 44 can rest on the stepped portion 43 and can be supported by the stepped portion 43 for a smooth transition between two driving surface modules 4. In other words, adjacent transport device units 1 (see FIG. 2) can be arranged such that, in each case, a side provided with an overhang portion 44 can contact a side provided with a stepped portion 43.

Further, for tolerance compensation in a vertical direction, resilient elements 450, 451 can be provided underneath the driving surface element 41 for forcing the stepped portion 43 towards the overhang portion 44. The resilient elements 450, 451, in the embodiment shown, can comprise pairs of hooked-shaped elements 450 arranged underneath each overhang portion 44, wherein each pair of hooked-shaped elements 450 can interact with a tongue-shaped element 451 provided at sides of the driving surface element 41 having a stepped portion 43. The tongue-shaped element 451 and the stepped portion 43 can be arranged between the overhang portion 44 and the hooked-shaped elements 450. Hence, wherein the overhang portion 44 and the hooked-shaped elements 450 can form a clamp for forcing the stepped portion 43 towards the overhang portion 44 and vice versa.

As best seen in FIG. 14, in the embodiment shown, a grid-shaped resilient component 45 can be provided, wherein the resilient elements 450, 451 can be formed at ends of grid-lines of the grid-shaped resilient component 45. Grid-lines of the grid-shaped resilient component 45 can be arranged above some of the actuators 30 of the actuator module 3 (see FIG. 2), wherein the grid-lines can have recesses 452 for receiving upper ends of the actuators 30. The grid-shaped resilient component 45 can be mounted to the bottom surface of the driving surface element 41. In the embodiment shown, the bottom surface of the driving surface element 41 can have screw sockets 410 for fixing the grid-shaped resilient component 45 to the driving surface element 41.

In order to avoid a liquid accidently spilled on the upper surface of the transport device from entering the transport device unit 1, a sealing cord 46 can be provided. In the embodiment shown, the sealing cord 46 can extend along two sides of the driving surface element 41, namely the sides provided with the overhang portion 44. The sealing cord 46 can be mounted at the respective sides to the rim 42. For this purpose, a groove for mounting of the sealing cord 46 can be provided. At the respective opposite sides, the rim 42 can have a sealing projection for contacting the sealing cord 46.

In order to ensure that the driving surface modules 4 are mounted in such an orientation that in each case a side having an overhang portion 44 can contact a side of a driving surface module 4 of an adjacent transport device unit 1 having a stepped portion 43, the driving surface element 40 can have no rotational symmetry and can be mounted only in one orientation.

Figure 16:
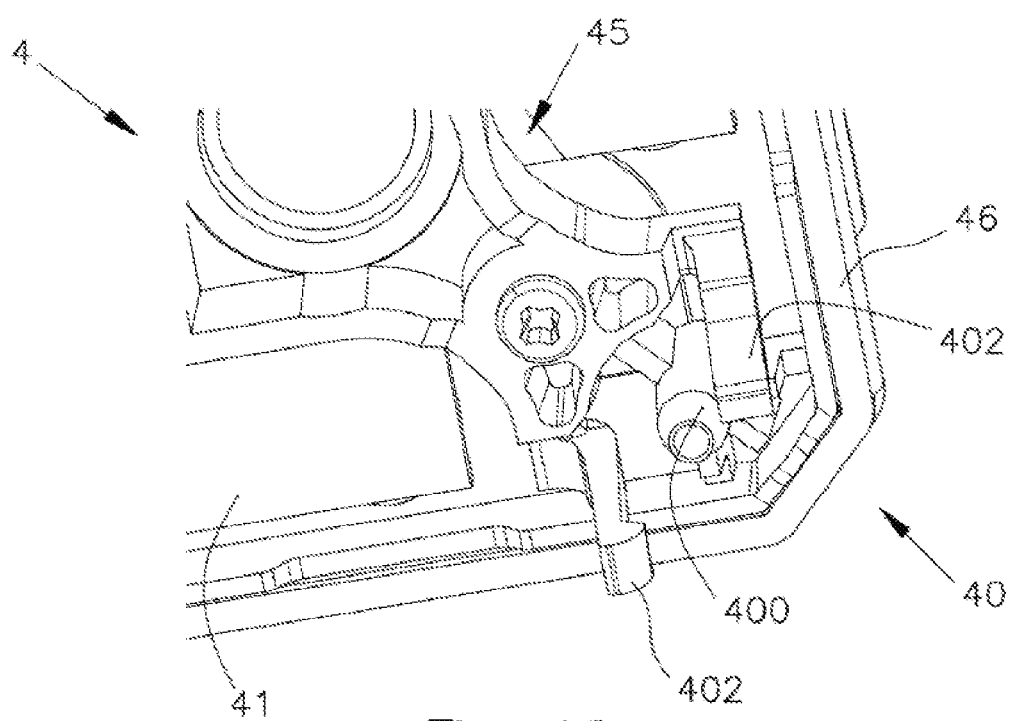
FIG. 16 illustrates a perspective view of a detail XVI of FIG. 14 according to an embodiment of the present disclosure.

FIG. 16 shows a detail XVI of FIG. 14, wherein the connecting structure 40 for connecting the driving surface module 4 with the corner support 5 (see FIG. 2) is shown in more detail. The connecting structure 40 can comprise a connection pin 400 formed integrally with the driving surface element 41. Further, two snap-fit elements 402 can be provided, which in the embodiment shown are formed integrally with the grid-shaped component 45.

Figure 17:
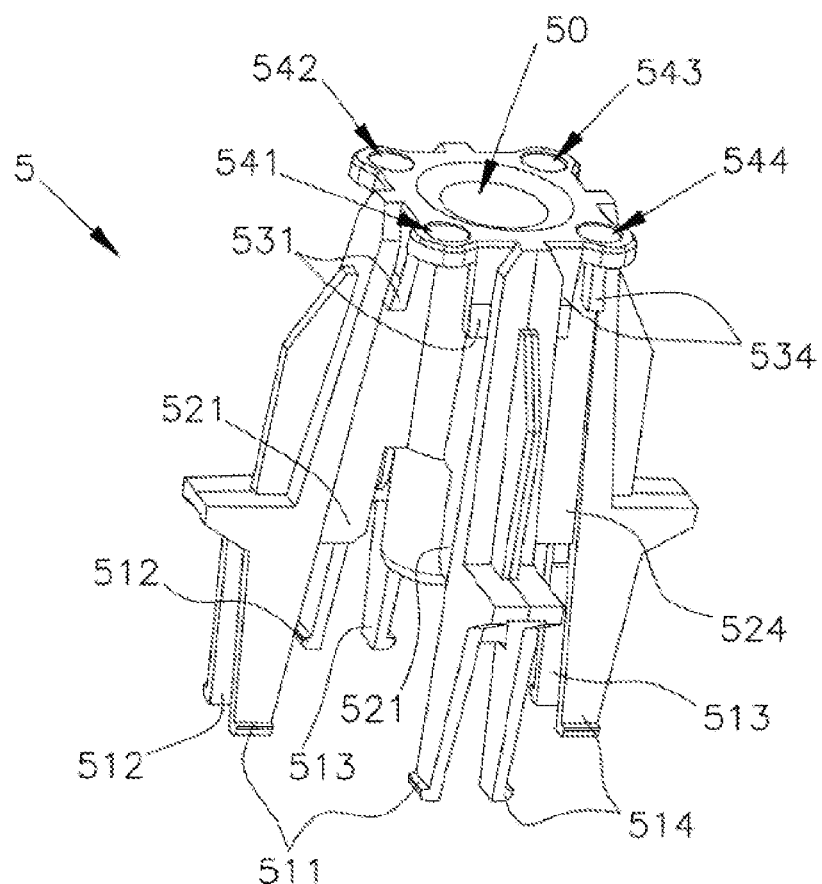
FIG. 17 illustrates a perspective view of a corner support of the transport device unit of FIG. 2 according to an embodiment of the present disclosure.

FIG. 17 is a perspective view of a corner support 5 for connecting adjacent transport device units 1 (see FIG. 1). The corner support 5, in the embodiment shown, can function as a cross-shaped connection node for both, a plurality of base plate modules 2 and a plurality of driving surface modules 4. As shown in FIGS. 2 and 3, the corner supports 5 can be arranged at the four corners of the transport device unit 1, wherein the driving surface module 4 can rest on the four corner supports 5. Each corner support 5 can have a liquid trap recess 50 at its center for collecting liquid accidently spilled on the driving surface.

Figure 18:
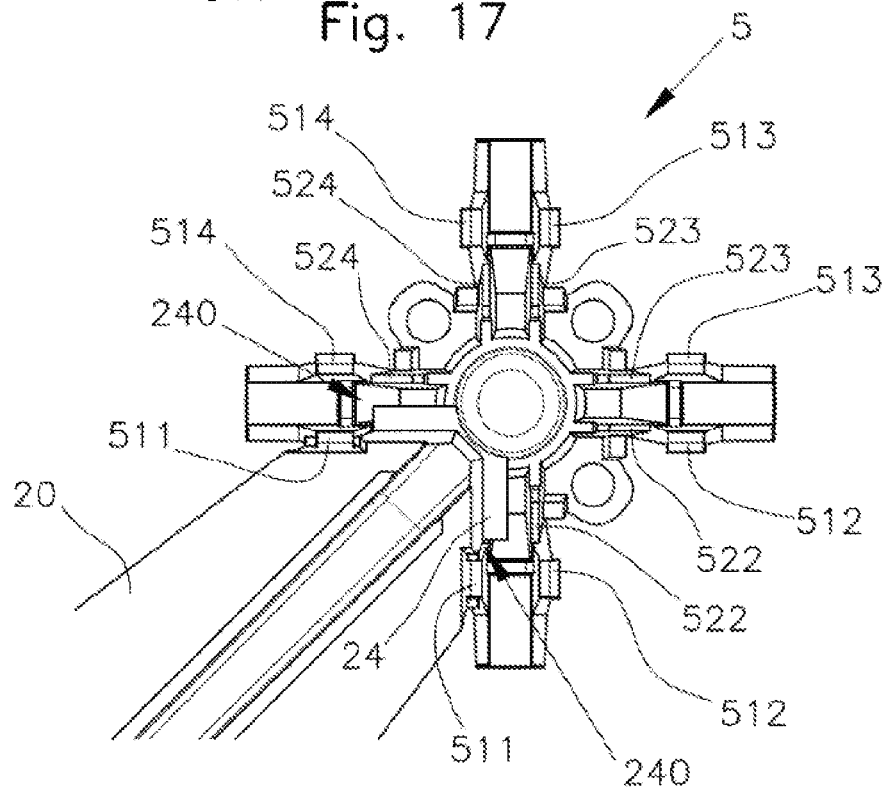
FIG. 18 illustrates a bottom view of a detail XVIII of FIG. 2 according to an embodiment of the present disclosure.

For connecting and aligning the four base plate modules 2, four pairs of snap-fit elements 511, 512, 513, 514 and four pairs of ribs 521, 522, 523, 524 (only partly visible in FIG. 17) can be provided. The snap-fit elements 511, 512, 513, 514, as well as the ribs 521, 522, 523, 524 of each pair, can be arranged at an angle of about 90° to each other. The ribs 521, 522, 523, 524 can be configured to enter into the longitudinal grooves 240 of the connecting bracket 24 of the base plate modules 2 (see FIG. 4) and the snap-fit elements 511, 512, 513, 514 can be configured to be snapped to a hook provided at a side of the connecting bracket 24 directly adjacent to this longitudinal groove 240. FIG. 18 shows a bottom view of a corner support 5 attached to a base plate 20, wherein ribs 521 (not visible in FIG. 18) can be inserted into longitudinal grooves 240 of the connecting bracket 24 of the base plate 20 and snap-fit elements 511 can be snapped to the hook provided at the side of the connecting bracket 24 directly adjacent to this longitudinal groove 240.

Figure 19:
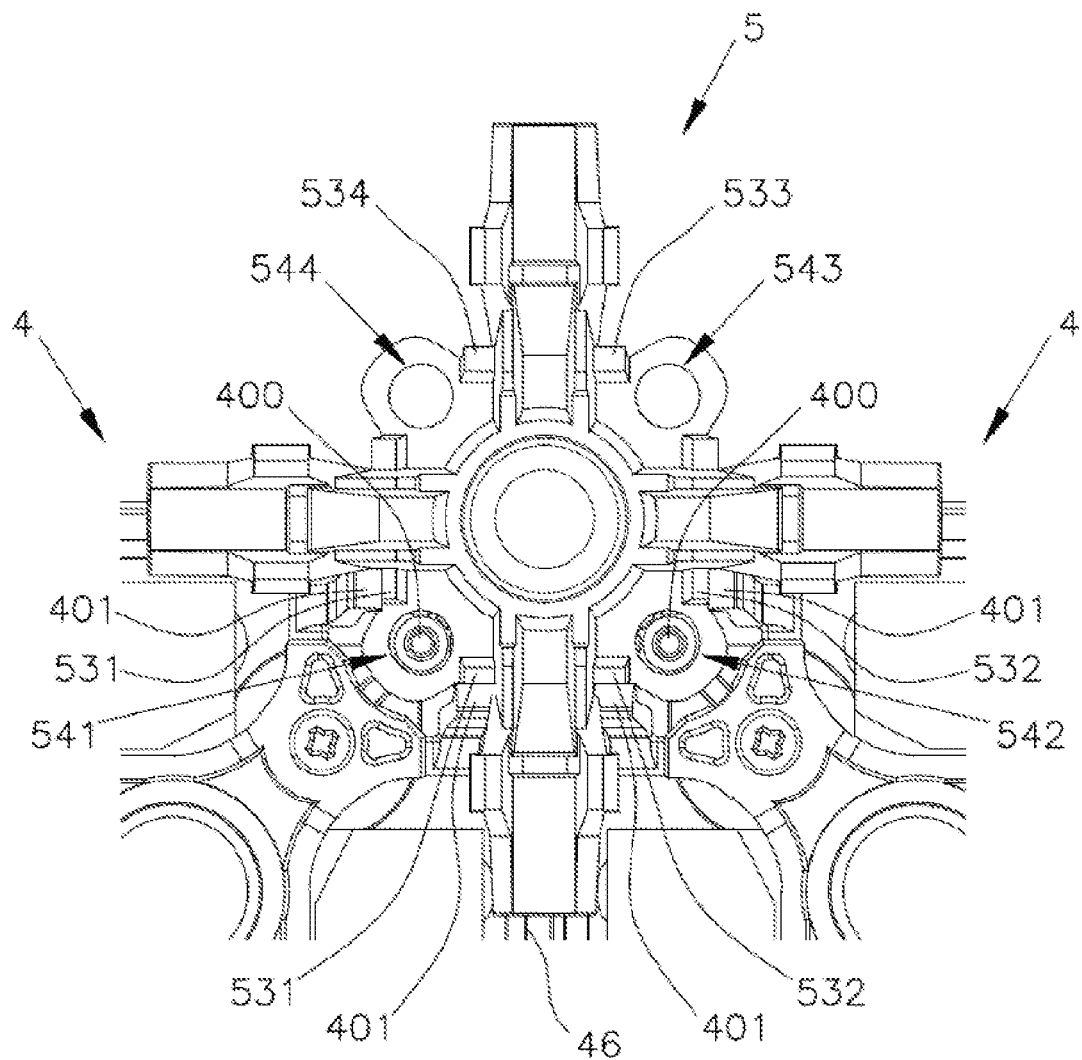
FIG. 19 illustrates a bottom view showing a detail of two adjacent driving surface modules of FIG. 13 connected by a corner support 5 according to an embodiment of the present disclosure.

The corner support 5 shown in FIG. 17 can further have four pairs of latch elements 531, 532, 533, 534 (only partly visible in FIG. 17) for connecting and aligning the four driving surface modules 4. The latch elements 531, 532, 533, 534 of each pair can also be arranged at an angle of about 90° to each other. Between the two latch elements 531, 532, 533, 534 of each pair, an opening 541, 542, 543, 544 can be provided. FIG. 19 shows a bottom view of a corner support 5, wherein two connecting structures 40 of two adjacent driving surface modules 4 can be coupled by the corner support 5. The connection pin 400 of each connecting structure 40 can be inserted into an opening 541, 542 and the snap-fit elements 402 of the respective connecting structure 40 can interlock with the latch elements 531. 532 arranged on either side of the respective opening 541, 542.

As mentioned above, a sealing cord 46 can be arranged between two adjacent driving surface modules 4.

Figure 20:
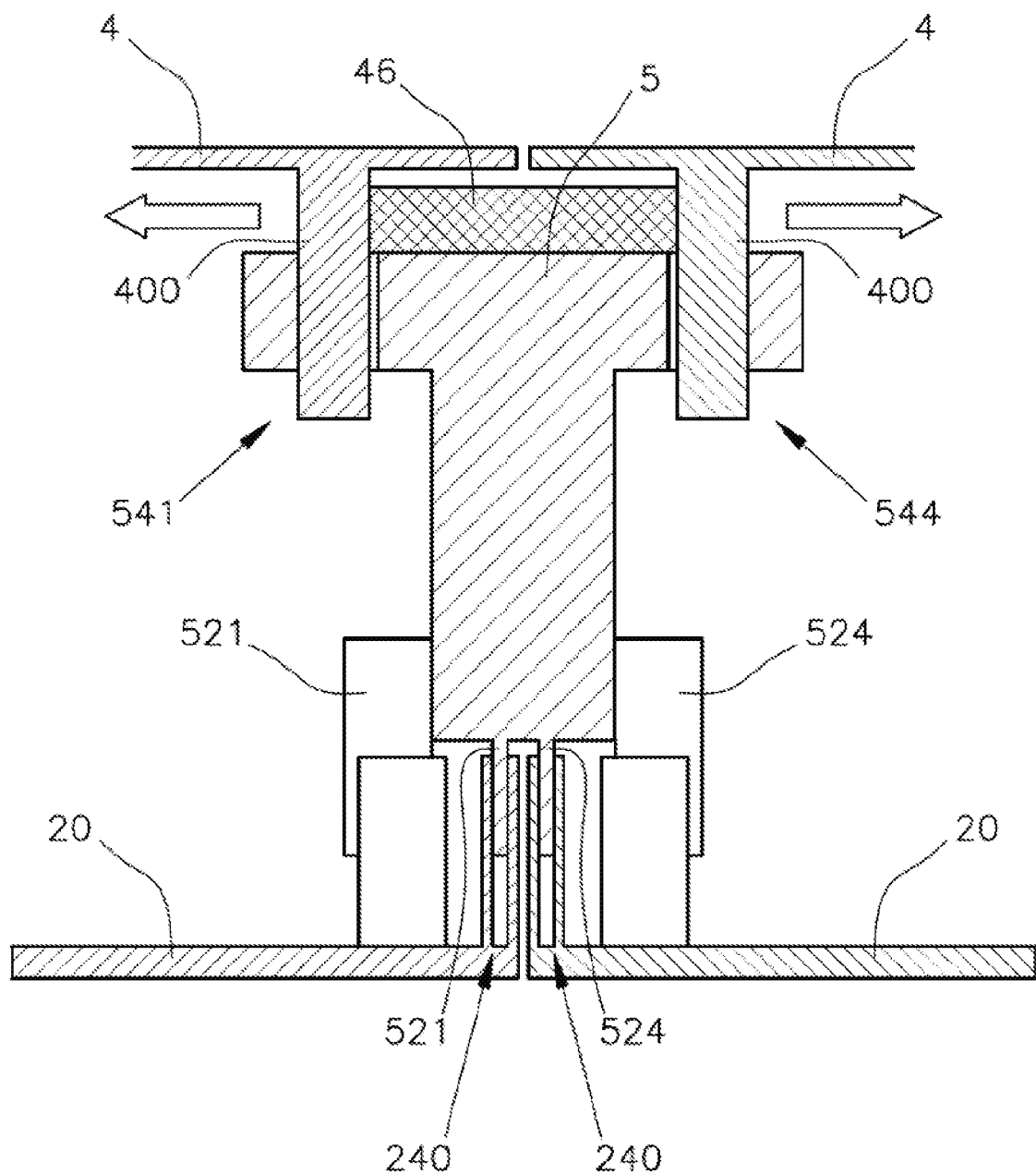
FIG. 20 illustrates a schematic sectional view showing two adjacent transfer units coupled by a corner support according to an embodiment of the present disclosure.

FIG. 20 schematically shows a sectional view of two adjacent transfer units with base plate elements 20 and driving surface modules 4, which can be coupled by a corner support 5.

The connection pins 400 of each driving surface module 4 can be inserted into an associated opening 541, 544 of a common corner support 5. As schematically shown in FIG. 20, the sealing cord 46 can force the two driving surface modules 4 apart, and hence, the connection pins 400 can be forced against the edges of the openings 541, 544 receiving the connection pins 400 as schematically shown by two arrows in FIG. 20. This can allow for a precise positioning of the adjacent driving surface modules 4 with respect to each other. Further, it can be avoided that acceptable tolerances between adjacent driving surface modules 4 accumulate along the driving surface.

As also shown in FIG. 20, the corner support 5 can also serve to clamp a base plate element 20 to an adjacent base plate element 20. For this purpose, in the embodiment shown, two substantially parallel ribs 521, 524 can be inserted into two substantially parallel arranged longitudinal grooves 240 of the brackets 24 of the adjacent base plate elements 20.

One advantage of the modular system can be that the transport device can be easily adapted to changing conditions and/or requirements of a laboratory automation system. Further, malfunctioning transport device units 1 such as, for example, malfunction actuator modules 3, can be easily and quickly replaced. The transport device units 1 can be arranged tightly at the transport device. For removal of a driving surface module 4, the driving surface module 4 can be raised at one side having an overhang portion 44 and inclined. An access to the actuator module 3 can be more challenging. For an easy removal, a removal tool 8 can be provided.

Figure 21:
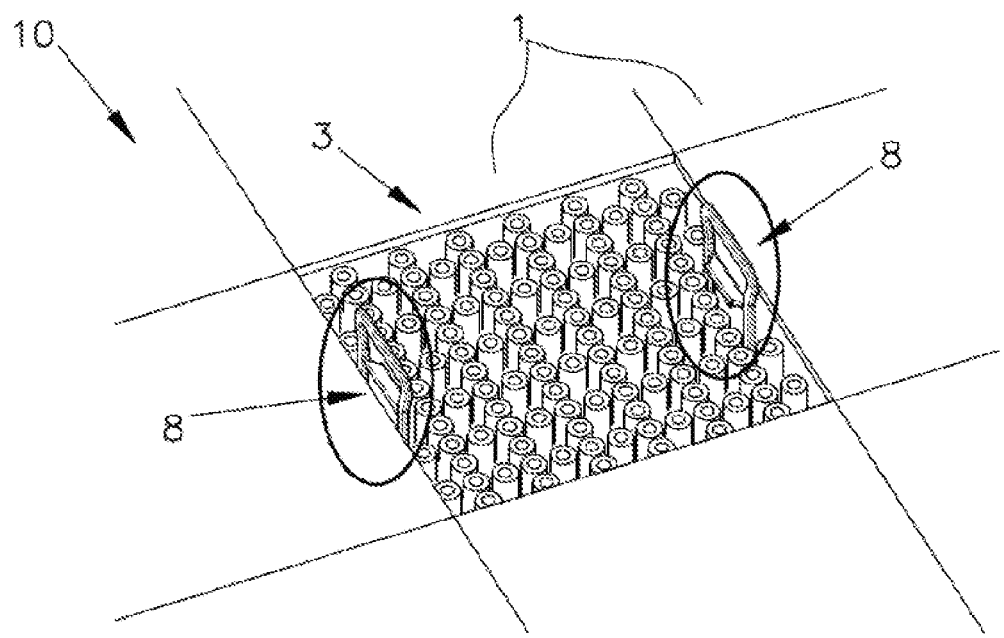
FIG. 21 illustrates a transport device upon removal of a transport device unit according to an embodiment of the present disclosure.
Figure 22:
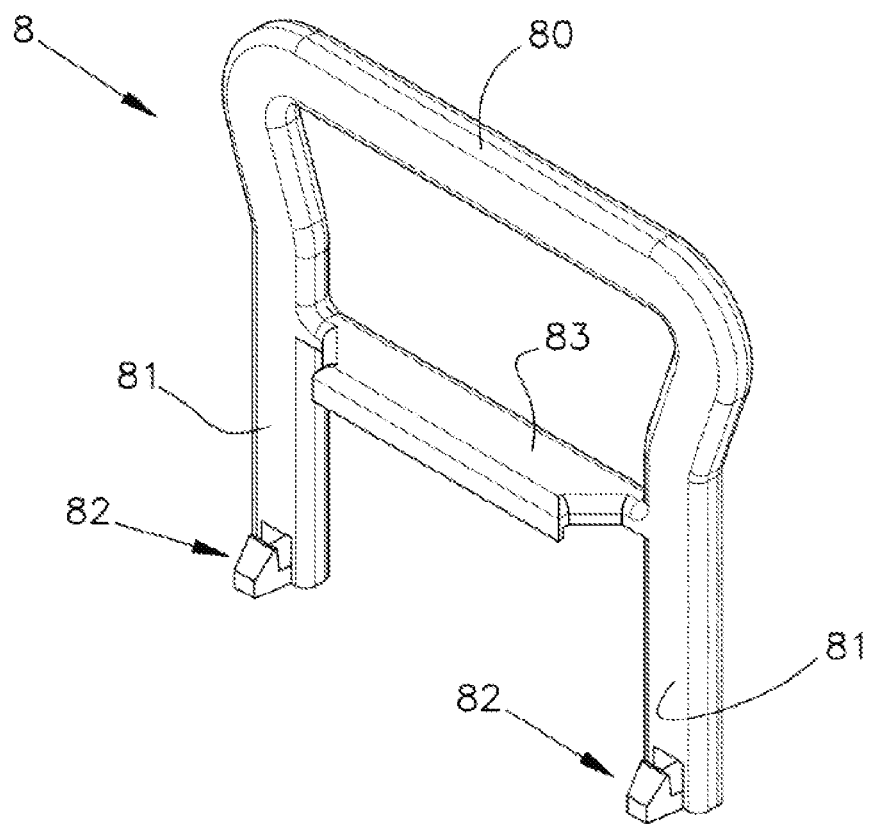
FIG. 22 illustrates a perspective of a tool for removing a transport device unit from a transport device according to an embodiment of the present disclosure.

FIG. 21 shows the transport device 10 upon removal of one actuator module 3 of a transport device unit 1 using two removal tools 8. FIG. 22 shows a removal tool 8 in a perspective view.

As shown in FIG. 21, for a removal of the actuator module 3, at first the driving surface module 4 can be removed. After the removal the driving surface module 4 as shown in FIG. 21, two removal tools can be inserted at two opposing sides of the actuator module 3.

The removal tool 8 can be substantially U-shaped with a handle portion 80 and two legs 81. The legs 81 can be configured for entering into the guiding grooves 38 of the actuator module 3 (see FIGS. 9 and 10). At the distal ends of the legs 81, engagement hooks 82 can be provided for engaging with a bottom surface 310 of the carrier element 31 of the actuator module 3 and/or hooks can be provided in the grooves 38 for removing the actuator module 3 from the transport device 10.

The removal tool 8 can be provided with a stop element 83 arranged at least substantially in parallel to the handle portion 80. The stop element 83 can prevent the removal tool 8 from entering the grooves 38 too deeply. Hence, an unintentional damaging of the actuator module 3 and/or any element arranged below the actuator module 3 with the removal tool 8 can be avoided.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A transport device unit for a transport device assembled using a plurality of transport device units, the transport device unit comprising:
   a base plate module with a base plate for fixing the transport device unit to a support frame;
   an actuator module with a plurality of electro-magnetic actuators, wherein the actuator module is supported by the base plate module;
   a driving surface module with a driving surface element, wherein the driving surface element is arranged above the actuator module covering the actuators and configured to carry sample container carriers; and
   a control device configured to control movement of the sample container carriers on top of the driving surface by driving the plurality of electro-magnetic actuators, wherein the base plate module and the actuator module have cooperating male and female coupling elements and wherein the male and female coupling elements assume shapes and/or are arranged for a mechanical coding not having rotational symmetry for ensuring a correct alignment of the base plate module and the actuator module.

2. The transport device unit according to claim 1, wherein the transport device unit has a tessellating basic shape.

3. The transport device unit according to claim 2, wherein the tessellating basic shape is a regular polygonal basic shape.

4. The transport device unit according to claim 1, wherein the driving surface module is detachably mounted to the base plate module.

5. The transport device unit according to claim 1, wherein the base plate has at least one aperture configured to allow a slot nut to be passed through for mounting the transport device unit to a support bar of the support frame by the slot nut.

6. The transport device unit according to claim 5, wherein at least two apertures are arranged at an angle of 90°.

7. The transport device unit according to claim 1, further comprises,
   a wiring board is mounted to the base plate, the wiring board having a board-to-board connector for an electrical and mechanical coupling with an actuator module wiring board of the actuator module.

8. The transport device unit according to claim 7, wherein the wiring board and the actuator module wiring board have cooperating centering elements and wherein the wiring board is float-mounted to the base plate.

9. The transport device unit according to claim 1, wherein the base plate has a recess for accommodating a fan and wherein at least one filter element is detachably mounted to insides of walls surrounding the recess.

10. The transport device unit according to claim 9, wherein the recess has a rectangular basic shape for accommodating the fan and wherein four separate filter elements are detachably mounted to insides of walls surrounding the recess.

11. The transport device unit according to claim 10, wherein the base plate has receiving slits for mounting the filter elements from below.

12. The transport device unit according to claim 1, wherein the actuator module has stands protruding from a bottom surface and serving as male coupling elements for coupling the actuator module to the base plate module.

13. The transport device unit according to claim 1, wherein the actuator module has an actuator module wiring board having sockets and a magnetically conductive structure and the actuators have contact pins and wherein the actuators are mounted to the magnetically conductive structure such that the contact pins are electrically and mechanically connected with the sockets.

14. The transport device unit according to claim 13, wherein the magnetically conductive structure has bearing pins configured to receive actuators having a core.

15. A transport device, the transport device comprising:
   a plurality of transport device units according to claim 1.

16. The transport device according to claim 15, wherein base plate modules of neighboring transport device units are coupled and aligned at their adjacent corners by corner supports.

17. A system, the system comprising:
   the transport device according to claim 15; and
   at least one a removal tool configured to be inserted between two actuator modules of neighboring transport device units, wherein the at least one removal tool and the actuator module have cooperating coupling elements.

18. A laboratory sample distribution system, the laboratory sample distribution system comprising:
- a transport device according to claim 15; and
- a plurality of sample container carriers, the sample container carriers each comprising at least one magnetically active device and configured to carry a sample container containing a sample.

19. The laboratory sample distribution system according to claim 18, wherein the at least one magnetically active device is at least one permanent magnet.

20. A laboratory automation system, the laboratory automation system comprising:
- a plurality of pre-analytical, analytical and/or post-analytical stations; and
- a laboratory sample distribution system according to claim 18.

* * * * *